United States Patent
Hubschwerlen et al.

(10) Patent No.: US 8,349,829 B2
(45) Date of Patent: Jan. 8, 2013

(54) [4-(1-AMINO-ETHYL)-CYCLOHEXYL]-METHYL-AMINE AND [6-(1-AMINO-ETHYL)-TETRAHYDRO-PYRAN-3-YL]-METHYL-AMINE DERIVATIVES AS ANTIBACTERIALS

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 215 days.

(21) Appl. No.: 12/996,360

(22) PCT Filed: Jun. 2, 2009

(86) PCT No.: PCT/IB2009/052307
§ 371 (c)(1),
(2), (4) Date: Dec. 3, 2010

(87) PCT Pub. No.: WO2009/147616
PCT Pub. Date: Dec. 10, 2009

(65) Prior Publication Data
US 2011/0082132 A1 Apr. 7, 2011

(30) Foreign Application Priority Data

Jun. 3, 2008 (WO) .................. PCT/IB2008/052157
Dec. 18, 2008 (WO) .................. PCT/IB2008/055421

(51) Int. Cl.
| | | |
|---|---|---|
| C07D 513/04 | (2006.01) | |
| C07D 498/04 | (2006.01) | |
| C07D 405/06 | (2006.01) | |
| A61K 31/542 | (2006.01) | |
| A61K 31/5383 | (2006.01) | |
| A61K 31/4709 | (2006.01) | |

(52) U.S. Cl. ............ 514/224.2; 514/230.5; 514/312; 514/302; 544/48; 544/105; 546/115; 546/153

(58) Field of Classification Search ............ 514/224.2, 514/230.5, 312, 302; 544/48, 105; 546/115, 546/153
See application file for complete search history.

(56) References Cited

FOREIGN PATENT DOCUMENTS

| | | |
|---|---|---|
| EP | 2 022 793 | 2/2009 |
| WO | WO 02/056882 | 7/2002 |
| WO | WO 2006/032466 | 3/2006 |
| WO | WO 2006/134378 | 12/2006 |
| WO | WO 2006/137485 | 12/2006 |
| WO | WO 2007/138974 | 12/2007 |
| WO | WO 2008/009700 | 1/2008 |
| WO | WO 2008/078305 | 7/2008 |
| WO | WO 2008/152603 | 12/2008 |

OTHER PUBLICATIONS

Cha et al. "Acyclic Stereocontrol Induced by Allylic Alkoxy Groups, Synthetic Applications of Stereoselective Dihydroxylation in Natural Product Synthesis," Chem. Rev. 95(6):1761-1795 (1995), downloaded from http://pubs.acs.org on Jan. 27, 2009.
Chang et al., "Triazolinones as a Nonpeptide Angiotensin II Antagonists. 1. Synthesis and Evaluation of Potent 2,4,5-Trisubstituted Triazolinones," J. Med. Chem., 36:2558-2568 (1993).
Dess et al., "Readily Accessible 12-I-5 Oxidant for the Conversion of Primary and Secondary Alcohols to Aldehydes and Ketones," J. Org. Chem., 48(22):4155-4156 (1983), downloaded from http://pubs.acs.org on Jan. 27, 2009.
Ferrarini et al., "Synthesis of 1,8-Naphtyridine Derivatives. Potential Antihypertensive Agents," J. Heterocyclic Chem., 23:501-504 (1986).
Gould, "Salt Selection for Basic Drugs," International J. of Pharmaceutics, 33:201-217 (1986).
Greene & Wuts, "Chapter 7—Protection for the Amino Group" in Protective Groups in Organic Synthesis, 3rd Ed., pp. 494-653 (1999).
Kolb et al., "Catalytic Asymmetric Dihydroxylation," Chem Rev. 94(8):2483-2547 (1994), downloaded from http://pubs.acs.org on Jan. 27, 2009.
Larock, "Comprehensive Organic Transformations: A Guide to Functional Group Preparations—2nd Edition," Section Alcohols and Phenols, pp. 1075-1110, Wiley, New York, (1999).
Ley et al., "Tetrapropylammonium Perruthenate, $Pr_4N^+RuO_4^-$, TPAP: A Catalytic Oxidant for Organic Synthesis," Synthesis, 7:639-666 (1994).

(Continued)

*Primary Examiner* — Kahsay T Habte
(74) *Attorney, Agent, or Firm* — Hunton & Williams LLP

(57) ABSTRACT

The invention relates to antibacterial compounds of formula I

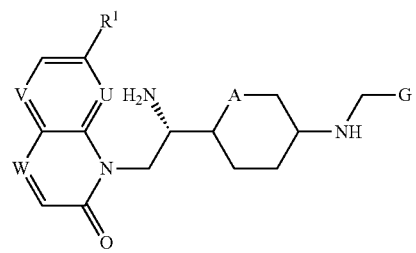

wherein
$R^1$ represents alkoxy or halogen;
U, V and W each represent CH, or one of U, V and W represents N and the others each represent CH;
A represents $CH_2$ or O;
G is CH═CH-E wherein E represents a phenyl group mono- or di-substituted with halogen, or G is a group of one of the formulae hereafter

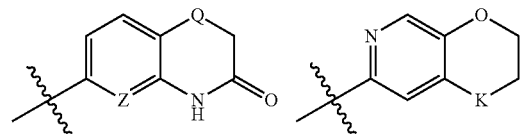

wherein Z represent CH or N, Q represents O or S and K represents O or S;
and salts of such compounds.

15 Claims, No Drawings

OTHER PUBLICATIONS

Mancuso et al., "Oxidation of Long-Chain and Related Alcohols to Carbonyls by Dimethyl Sulfoxide 'Activated' by Oxalyl Chloride," J. Org. Chem, 43(12):2480-2482 (1978), downloaded from http://pubs.acs.org on Jan. 27, 2009.

Mitsunobu, "The Use of Diethyl Azodicarboxylate and Triphenylphosphine in Synthesis and Transformation of Natural Products," Synthesis, No. 01. (1981), pp. 1-28.

Remington, The Science and Practice of Pharmacy, 21st Edition (2005), Contents pages identifying Part 5, Pharmaceutical Manufacturing.

Sato et al., One-pot Reductive Amination of Aldehydes and Ketones with a-picoline-borane in Methanol, in Water, and in Neat Conditions, Tetrahedron, 60:7899-7906 (2004).

Schaus et al., "Highly Selective Hydrolytic Kinetic Resolution of Terminal Epoxides Catalyzed by Chiral (salen)Co$^{III}$ Complexes. Practical Synthesis of Enantioenriched Terminal Epoxides and 1,2-Diols," J. Am. Chem. Soc., 124(7):1307-1315 (2002).

Shi, "Organocatalytic Asymmetric Epoxidation of Olefins by Chiral Ketones," Acc. Chem Res., 37:488-496 (2004).

Svetlik et al., "Condensation of (2-Bromo-1-phenylethylidene)malonitrile with Substituted Thioureas: An Unusual Ring Size Effect," J. Org. Chem., 55:4740-4744 (1990).

Talbot et al., "Bad Bugs Need Drugs: An Update on the Development Pipeline from the Antimicrobial Availability Task Force of the Infectious Diseases Society of America," Clinical Infectious Disease, 42:657-668 (2006).

Tokunaga et al., "Asymmetric Catalysis with Water: Efficient Kinetic Resolution of Terminal Epoxides by Means of Catalytic Hydrolysis," Science, 77:936-938 (1997).

International Search Report of PCT/IB2009/052307 mailed Nov. 17, 2009.

Notification Concerning Transmittal of International Preliminary Report on Patentability (Chapter 1 of the PCT) and Written Opinion mailed Dec. 16, 2010.

[4-(1-AMINO-ETHYL)-CYCLOHEXYL]-METHYL-AMINE AND [6-(1-AMINO-ETHYL)-TETRAHYDRO-PYRAN-3-YL]-METHYL-AMINE DERIVATIVES AS ANTIBACTERIALS

CROSS-REFERENCE TO RELATED APPLICATIONS

This application is the national phase application of PCT/IB2009/052307, filed Jun. 2, 2009, which claims the benefit of PCT/IB2008/052157, filed Jun. 3, 2008, and PCT/IB2008/055421, filed Dec. 18, 2008, the contents of each are hereby incorporated by reference in their entirety.

FIELD OF THE INVENTION

The present invention concerns [4-(1-amino-ethyl)-cyclohexyl]-methyl-amine and [6-(1-amino-ethyl)-tetrahydro-pyran-3-yl]-methyl-amine derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus*, *Streptococcus pneumoniae*, *Enterococcus* spp., and *Pseudomonas aeruginosa*, major sources of infections, are becoming multi-drug resistant and therefore difficult if not impossible to treat:
- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

Furthermore, the incidence of multi-drug-resistant Gram-negative strains such as *Enterobacteriacea* and *Pseudomonas aeruginosa*, is steadily increasing and new emerging organisms like *Acinetobacter* spp., which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (*Clinical Infectious Diseases* (2006), 42657-68).

In addition, microorganisms that are causing persistent infections are increasingly being recognized as causative agents or cofactors of severe chronic diseases like peptic ulcers or heart diseases.

WO 2006/134378 describes notably antibacterial compounds of formulae (A1) and (A2)

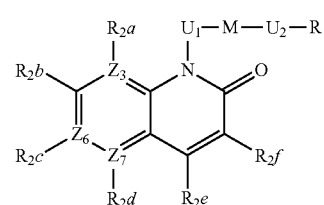

(A1)

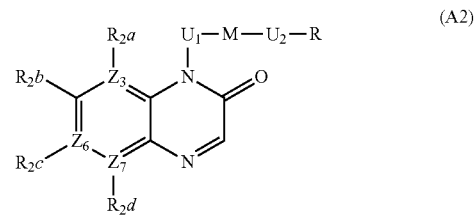

(A2)

wherein $Z_3$, $Z_6$ and $Z_7$ are C or N provided that when $Z_3$, $Z_6$ or $Z_7$ is N then $R_2a$, $R_2c$ or $R_2d$ is absent;

$R_2a$, $R_2b$, $R_2c$ and $R_2d$ may each independently represent (notably) H, fluoro, chloro or $(C_1$-$C_6)$alkoxy;

"----" is a bond or is absent;

Z is CH or N when "----" is a bond, or Z is O or NH when "----" is absent;

$U_1$ may represent CRaRb-CRcRd wherein Ra, Rb, Rc and Rd may each independently represent H or $(C_1$-$C_6)$alkyl;

M may notably represent the group

wherein Y may notably be $CH_2$ or O;

$U_2$ may notably represent NH—$CH_2$;

R may notably represent aryl or heteroaryl which may be optionally substituted on carbon; and any of L, $U_1$, M, $U_2$ and R may optionally be substituted on carbon by one to three substituents selected from (notably) halo, oxo or amino.

However WO 2006/134378 does not specifically disclose any compounds having an amino group attached to the $U_1$ radical.

WO 2006/137485, WO 2007/138974 and WO 2008/009700 describe similar antibacterial compounds based on a 1H-quinolin-2-one, 1H-quinoxalin-2-one or 1H-[1,5]naphthyridin-2-one motif. Again, no compounds of this type having an amino group attached to the middle chain are described in these documents.

The instant invention provides further antibacterial compounds based on a 1H-quinolin-2-one, 1H-quinoxalin-2-one, 1H-[1,5]naphthyridin-2-one or 1H-[1,8]naphthyridin-2-one motif.

DETAILED DESCRIPTION OF PREFERRED EMBODIMENTS

Various embodiments of the invention are presented hereafter:

i) The invention firstly relates to compounds of formula I

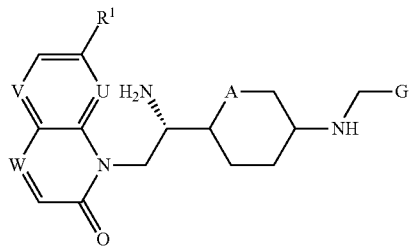

wherein
R¹ represents alkoxy or halogen;
U, V and W each represent CH, or one of U, V and W represents N and the others each represent CH;
A represents $CH_2$ or O;
G is CH=CH-E wherein E represents a phenyl group mono- or di-substituted with halogen (notably fluorine), or G is a group of one of the formulae hereafter

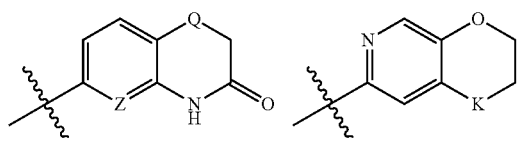

wherein Z represents CH or N, Q represents O or S and K represents O or S;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tert-butyl. The term "$(C_1-C_x)$alkyl" (x being an integer) refers to a straight or branched chain alkyl group containing 1 to x carbon atoms.

The term "alkoxy", used alone or in combination, refers to a saturated straight or branched chain alkoxy group containing from one to four carbon atoms. Representative examples of alkoxy groups include methoxy, ethoxy, propoxy, iso-propoxy, n-butoxy, iso-butoxy, sec-butoxy and tert-butoxy. The term "$(C_1-C_x)$alkoxy" refers to a straight or branched chain alkoxy group containing 1 to x carbon atoms.

The term "halogen" refers to fluorine, chlorine, bromine or iodine, preferably to fluorine or chlorine.

In this text, a bond interrupted by a wavy line shows a point of attachment of the radical drawn to the rest of the molecule. For example, the radical drawn below

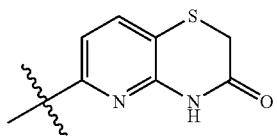

is the 3-oxo-3,4-dihydro-2H-pyrido[3,2-b][1,4]thiazine-6-yl group.

The term "pharmaceutically acceptable salts" refers to non-toxic, inorganic or organic acid and/or base addition salts. Reference can be made to "Salt selection for basic drugs", *Int. I Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention thus notably relates to compounds of formula I according to embodiment i) that are such that U represents CH and that G is CH=CH-E wherein E represents a phenyl group mono- or di-substituted with halogen (notably fluorine), or G is a group of the formula

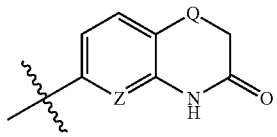

wherein Z represents CH or N and Q represents O or S;
and to salts (in particular pharmaceutically acceptable salts) of such compounds of formula I.

iii) In particular, the invention relates to compounds of formula I according to embodiment i) that are also compounds of formula $I_{CE}$

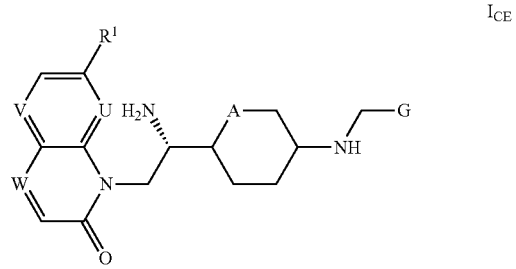

wherein
R¹ represents alkoxy or fluorine (notably alkoxy and especially methoxy);
U, V and W each represent CH, or U represents CH, one of V and W represents N and the other represents CH, or also U represents N and V and W each represent CH;

A represents CH$_2$ or O;

G is CH=CH-E wherein E represents a phenyl group di-substituted with halogen (notably di-substituted with fluorine), or G is a group of one of the formulae hereafter

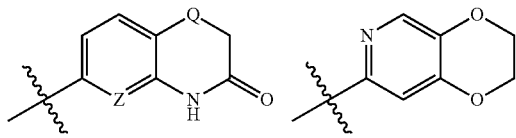

wherein Z represents CH or N and Q represents O or S;

and to salts (in particular pharmaceutically acceptable salts) of compounds of formula I$_{CE}$.

iv) The invention thus notably relates to compounds of formula I$_{CE}$ according to embodiment iii) that are such that U represents CH, V and W each represent CH, or one of V and W represents N and the other represents CH, and G is CH=CH-E wherein E represents a phenyl group di-substituted with halogen (notably di-substituted with fluorine), or G is a group of the formula

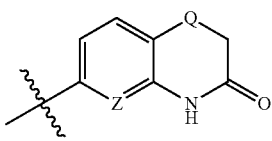

wherein Z represents CH or N and Q represents O or S;

and to salts (in particular pharmaceutically acceptable salts) of such compounds of formula I$_{CE}$.

v) According to a preferred embodiment of this invention, the compounds of formula I as defined in one of embodiments i) to iv) above or their salts (among which the pharmaceutically acceptable salts will be preferred) will be such that R$^1$ is (C$_1$-C$_4$)alkoxy or fluorine (and preferably (C$_1$-C$_3$)alkoxy, in particular methoxy or ethoxy, especially methoxy).

vi) According to a main embodiment of this invention, the compounds of formula I as defined in one of embodiments i) to v) above or their salts (among which the pharmaceutically acceptable salts will be preferred), will be such that U represents CH.

vii) In a particular sub-embodiment of this invention, the compounds of formula I as defined in embodiment vi) above or their salts (among which the pharmaceutically acceptable salts will be preferred) will be such that V and W each represent CH.

viii) In another particular sub-embodiment of this invention, the compounds of formula I as defined in embodiment vi) above or their salts (among which the pharmaceutically acceptable salts will be preferred) will be such that one of V and W represents N and the other represents CH.

ix) According to one variant of sub-embodiment viii), the compounds of formula I as defined in embodiment viii) above or their salts (among which the pharmaceutically acceptable salts will be preferred) will be such that V represents N and W represents CH.

x) According to the other variant of sub-embodiment viii), the compounds of formula I as defined in embodiment viii) above or their salts (among which the pharmaceutically acceptable salts will be preferred) will be such that V represents CH and W represents N.

xi) According to another main embodiment of this invention, the compounds of formula I as defined in one of embodiments i) to v) above or their salts (among which the pharmaceutically acceptable salts will be preferred) will be such that U represents N.

xii) Preferably, the compounds of formula I as defined in embodiment xi) above or their salts (among which the pharmaceutically acceptable salts will be preferred) will be such that V and W each represent CH.

xiii) In a general manner, the compounds of formula I as defined in embodiment i) above or their salts (among which the pharmaceutically acceptable salts will be preferred) will preferably be such that U, V and W each represent CH, or U and W each represent CH and V represents N, or U and V each represent CH and W represents N, or also U represents N and V and W each represent CH (whereby R$^1$ will preferably be (C$_1$-C$_4$)alkoxy or fluorine, and more preferably (C$_1$-C$_3$)alkoxy, in particular methoxy or ethoxy, especially methoxy).

xiv) According to one main variant of this invention, the compounds of formula I as defined in one of embodiments i) to xiii) above or their salts (among which the pharmaceutically acceptable salts will be preferred) will be such that A represents CH$_2$.

xv) According to the other main variant of this invention, the compounds of formula I as defined in one of embodiments i) to xiii) above or their salts (among which the pharmaceutically acceptable salts will be preferred) will be such that A represents O.

xvi) According to one main embodiment of this invention, the compounds of formula I as defined in one of embodiments i) to xv) above or their salts (among which the pharmaceutically acceptable salts will be preferred) will be such that G is a group of the formula CH=CH-E (whereby the double bond of said group is preferably in (E) configuration).

xvii) Preferably, the compounds of formula I as defined in embodiment xvi) above or their salts (among which the pharmaceutically acceptable salts will be preferred) will be such that E represents a phenyl group di-substituted with halogen (notably di-substituted with fluorine, for example 2,5-difluorophenyl).

xviii) According to another main embodiment of this invention, the compounds of formula I as defined in one of embodiments i) to xv) above or their salts (among which the pharmaceutically acceptable salts will be preferred) will be such that G is a group of the formula

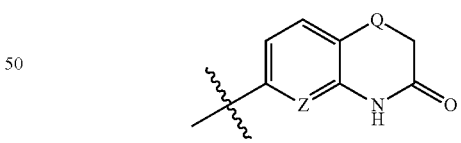

wherein Z represents CH or N and Q represents O or S.

xix) Preferably, the compounds of formula I as defined in embodiment xviii) above or their salts (among which the pharmaceutically acceptable salts will be preferred) will be such that Z represents CH and Q represents O or such that Z represents N and Q represents O or S (notably such that Z represents N and Q represents O or S).

xx) According to yet another main embodiment of this invention, the compounds of formula I as defined in one of embodiments i) to xv) above or their salts (among which the pharmaceutically acceptable salts will be preferred) will be such that G is a group of the formula

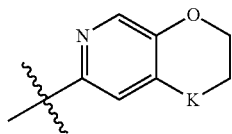

wherein K represents O or S (and preferably O).

xxi) In a general manner, the compounds of formula I as defined in embodiment i) or iii) above or in the combination of embodiment i) or iii) with any of embodiments v) to xv), or their salts (among which the pharmaceutically acceptable salts will be preferred), will preferably be such that G represents 3-oxo-3,4-dihydro-2H-benzo[1,4]oxazin-6-yl, 3-oxo-3,4,4a,8a-tetrahydro-2H-pyrido[3,2-b][1,4]thiazin-6-yl, 3-oxo-3,4,4 a, 8a-tetrahydro-2H-pyrido[3,2-b][1,4]oxazin-6-yl, 2,3-dihydro-[1,4]dioxino[2,3-c]pyridin-7-yl or 2-(2,5-difluoro-phenyl)-vinyl (and notably 3-oxo-3,4-dihydro-2H-benzo[1,4]oxazin-6-yl, 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl or 2-(2,5-difluoro-phenyl)-vinyl).

xxii) Also in a general manner, the compounds of formula I as defined in embodiment ii) or iv) above or in the combination of embodiment ii) or iv) with any of embodiments v) to x), xiv) and xv), or their salts (among which the pharmaceutically acceptable salts will be preferred), will preferably be such that G represents 3-oxo-3,4-dihydro-2H-benzo[1,4]oxazin-6-yl, 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl or 2-(2,5-difluoro-phenyl)-vinyl.

xxiii) Besides, the compounds of formula I as defined in one of embodiments i) to xxii) above or their salts (among which the pharmaceutically acceptable salts will be preferred) will preferably be such that that they possess the following stereochemistry:

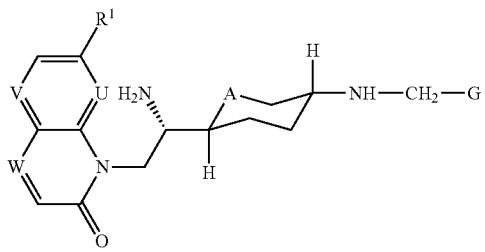

In other words, the compounds of formula I as defined in one of embodiments i) to xxii) above or their salts (among which the pharmaceutically acceptable salts will be preferred) will preferably be such that the non-hydrogen side chains of the cyclohexane or tetrahydropyrane ring are in trans-configuration. Thus, in the particular case wherein A represents O, the absolute stereochemistry of the tetrahydropyrane ring will preferably be (2S,5R).

xxiv) Particularly preferred are the following compounds of formula I as defined in embodiment i) or iii):

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]thiazin-3-one;

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]oxazin-3-one;

6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]oxazin-3-one;

1-((2S)-2-amino-2-{(2S,5R)-5-[(E)-3-(2,5-difluoro-phenyl)-allylamino]-tetrahydro-pyran-2-yl}-ethyl)-7-methoxy-1H-quinolin-2-one;

6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-benzo[1,4]oxazin-3-one;

6-({(3R,6S)-6-[(1S)-1-amino-2-(7-methoxy-2-oxo-2H-quinoxalin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]oxazin-3-one;

1-((1S)-2-amino-2-{(2S,5R)-5-[(2,3-dihydro-[1,4]dioxino[2,3-c]pyridin-7-ylmethyl)-amino]-tetrahydro-pyran-2-yl}-ethyl)-7-methoxy-1H-[1,8]naphthyridin-2-one;

1-((1R)-2-amino-2-{4-[(E)-3-(2,5-difluoro-phenyl)-allylamino]-cyclohexyl}-ethyl)-7-methoxy-1H-quinolin-2-one;

as well as the salts (in particular the pharmaceutically acceptable salts) thereof, whereby the first 9 compounds and their salts (in particular their pharmaceutically acceptable salts) constitute a particular sub-embodiment.

The compounds of formula I according to the invention, i.e. according to one of embodiments i) to xxiv), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtherias*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bar-* tonella henselae; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acinetobacter baumanii, Stenothrophomonas maltophilia, Neisseria meningitidis, Bacillus cereus, Bacillus anthracis, Corynebacterium* spp., *Propionibacterium acnes* and bacteroide spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I according to this invention, or the pharmaceutically acceptable salt thereof, may be used for the preparation of a medicament, and are suitable, for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations:
The following abbreviations are used throughout the specification and the examples:
Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
aq. aqueous
br. broad
Boc tert-butoxycarbonyl
Cbz benzyloxycarbonyl
CC column chromatography over silica gel
DEAD diethyl azodicarboxylate
DCE 1,2-dichloroethane
DCM dichloromethane
$(DHQD)_2PYR$ hydroquinidine 2,5-diphenyl-4,6-pyrimidinediyldiether
DIAD diisopropyl azodicarboxylate
DIPE diisopropylether
DIPEA N,N-diisopropylethylamine
DMAP 4-dimethylaminopyridine
DME 1,2-dimethoxyethane
DMF N,N-dimethylformamide
DMSO dimethylsulfoxide
DPPA diphenyl phosphoryl azide
EA ethyl acetate
ESI Electron Spray Ionisation
eq. equivalent
ether diethyl ether
Et ethyl
EtOH ethanol
Fmoc 9-fluorenylmethoxycarbonyl
Hex hexane
Hept heptane
HV high vacuum conditions
LiHMDS lithium hexamethyldisilazide
MCPBA meta-chloroperbenzoic acid
Me methyl
MeOH methanol MS Mass Spectroscopy
Ms methanesulfonyl (mesyl)
NMO N-methyl-morpholine N-oxide
org. organic
Pd/C palladium on carbon
Pd(OH)$_2$/C palladium dihydroxide on carbon
Ph phenyl
Piv pivaloyl
PTT phenyltrimethylammonium tribromide
Pyr pyridine
quant. quantitative
rac. racemic
rt room temperature
sat. saturated
tBu tert-butyl
TEA triethylamine
Tf trifluoromethanesulfonyl (triflyl)
TFA trifluoroacetic acid
THF tetrahydrofuran
TMSCl trimethylsilyl chloride
Ts para-toluenesulfonyl
wt % weight percent
% v/v volume percent General Reaction Techniques:

General Reaction Technique 1: Amine Protection:

Amines are usually protected as carbamates such as Alloc, Cbz, Boc or Fmoc. They are obtained by reacting the amine with allyl or benzyl chloroformate, di tert-butyl dicarbonate or Fmoc-Cl in presence of a base such as NaOH, TEA, DMAP or imidazole. They can also be protected as N-benzyl derivatives by reaction with benzyl bromide or chloride in presence of a base such as Na$_2$CO$_3$ or TEA. Alternatively, N-benzyl derivatives can be obtained through reductive amination in presence of benzaldehyde and a borohydride reagent such as NaBH$_4$, NaBH$_3$CN or NaBH(OAc)$_3$ in a solvent such as EtOH. Further strategies to introduce other amine protecting groups have been described in *Protecting Groups in Organic Synthesis,* 3$^{rd}$ Ed (1999), 494-653; T. W. Greene, P. G. M. Wuts (Publisher: John Wiley and Sons, Inc., New York, N.Y.).

General Reaction Technique 2: Reductive Amination:

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, TRF, DCM or DCE or mixture of solvents such as MeOH-DCE. The reaction can be catalyzed by traces of acid (usually AcOH). The intermediate imine is reduced with a suitable reducing agent (e.g. NaBH$_4$, NaBH$_3$CN, or NaBH(OAc)$_3$ or through hydrogenation over a noble catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906). In the particular case of ammonia, ammonium acetate can be used as a surrogate and the preferred reducing agent in this case is NaBH$_3$CN.

General Reaction Technique 3: Mitsunobu Reaction:

The alcohol is reacted with different nucleophiles such as phthalimide, DPPA or hydrazoic acid, generated from NaN$_3$ in acidic medium, in presence of PPh$_3$ and DEAD or DIAD in a solvent such as THF, DMF, DCM or 1,2-DME between −20° C. and 60° C. as reviewed by O. Mitsunobu, in *Synthesis* (1981), 1.

General Reaction Technique 4: Oxidation of Alcohols:

The alcohols can be transformed into their corresponding aldehydes or ketones by oxidation under Swern (see D. Swern et al., *J. Org. Chem.* (1978), 43, 2480-2482), Dess Martin (see D. B. Dess and J. C. Martin, *J. Org. Chem.* (1983), 48, 4155) or Ley (using tetrapropylammonium perruthenate see *Synthesis* (1994), 7, 639-66) conditions, respectively.

General Reaction Technique 5: Amino Deprotection:

The benzyl carbamates are deprotected by hydrogenolysis over a noble catalyst (e.g. Pd/C or Pd(OH)$_2$/C). The Boc group is removed under acidic conditions such as HCl in an organic solvent such as MeOH or dioxane, or TFA neat or diluted in a solvent such as DCM. The Fmoc group is removed by treatment with an organic base such as piperidine or morpholine in a solvent such as DMF. Further general methods to remove amine protecting groups have been described in *Protecting Groups in Organic Synthesis,* 3$^{rd}$ Ed (1999), 494-653; T. W. Greene, P. G. M. Wuts (Publisher: John Wiley and Sons, Inc., New York).

General Reaction Technique 6: Reduction of Aldehydes or Ketones into Their Corresponding Alcohols:

The aldehydes or ketones can be reduced to the corresponding alcohols using a variety of reducing agents as reviewed by Larock, R. C. in *Comprehensive Organic Transformations A guide to Functional Group Preparations,* 2$^{nd}$ Ed., Wiley, New York, Chichester, Weinheim, Brisbane, Singapore, Toronto (1999), Section Alcohols and phenols; p. 1075 to 1110. Among them LiAlH$_4$ and NaBH$_4$ are the most preferred.

General Reaction Technique 7: Alcohol Activation:

The alcohol is reacted with MSCl, TfCl or TsCl in presence of a base such as TEA in a dry aprotic solvent such as Pyr, THF or DCM between −30° C. and +50° C. In the case of the trifluoromethanesulfonate or methanesulfonate, Tf$_2$O or Ms$_2$O can also be used. These sulfonates can be reacted with NaI in acetone between +40° C. and +80° C. delivering the corresponding iodo derivatives.

General Reaction Technique 8: Obtaining Amines from Azides:

The azides are hydrogenated over a noble metal catalyst such as Pd/C in solvent such as MeOH or EA. Other reducing agents such as SnCl$_2$ in MeOH or Zn in AcOH can also be used. The reduction can also be performed using PPh$_3$ in presence of water as described in *J. Med. Chem.* (1993), 36, 2558-68.

General Reaction Technique 9: Cis-Dihydroxylation:

The diol is obtained by dihydroxylation of the corresponding ethylenic derivative using a catalytic amount of osmium tetroxide in the presence a co-oxidant such as NMO in an aq. solvent such as an acetone-water or DCM-water mixture (see Cha, J. K. *Chem. Rev.* (1995), 95, 1761-1795). The chiral cis-diols are obtained by using AD-mix α or AD-mix β in presence of methanesulfonamide in a water/2-methyl-2-propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to d) hereafter describe general methods for preparing compounds of formula I. The preparation of elaborated intermediates and basic building blocks is described thereafter. General synthetic methods used repeatedly throughout the schemes below are referenced to and described in the end of this section. If not indicated otherwise, the generic groups or integers U, V, W, R$^1$, A and G are as defined for formula I.

a) The compounds of formula I can be obtained by deprotecting the compounds of formula II

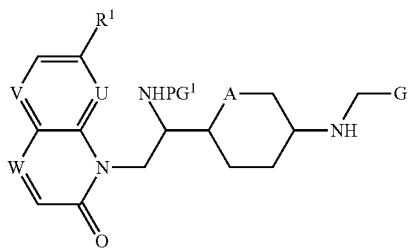

wherein PG$^1$ is an amino protecting group (such as Boc, Fmoc or Cbz) following general reaction technique 5.

b) The compounds of formula I can be obtained by reducing the compounds of formula III

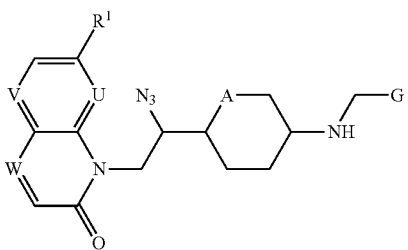

following general reaction technique 8.

c) The compounds of formula I can be obtained by reacting the compounds of formula IV

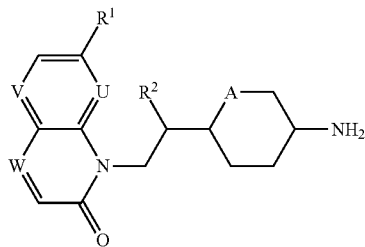

wherein R$^2$ is N$_3$ or NHBoc with an aldehyde of formula G-CHO using general reaction technique 2 followed, in the case wherein R$^2$ is NHBoc, by removal of the protecting group using general reaction technique 5, or, in the case wherein R$^2$ is N$_3$, by transformation of the azido group into an amino group using general reaction technique 8.

d) The compounds of formula I can be obtained by reacting the compounds of formula V

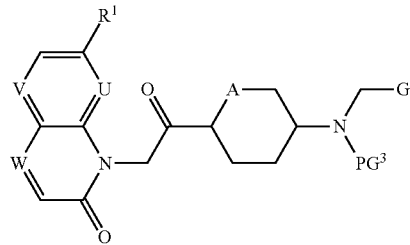

with ammonium acetate according to general reaction technique 2 followed by removal of the amino protecting group according to general reaction technique 5.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diasteromers they may be separated by an appropriate combination of silica gel chromatography, HPLC and crystallization techniques.

Preparation of the Synthesis Intermediates:

The compounds of formulae II and IV can be prepared as described in Scheme 1 hereafter.

Scheme 1

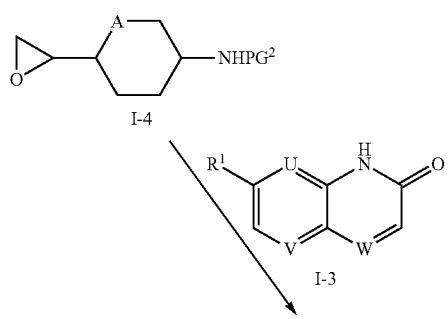

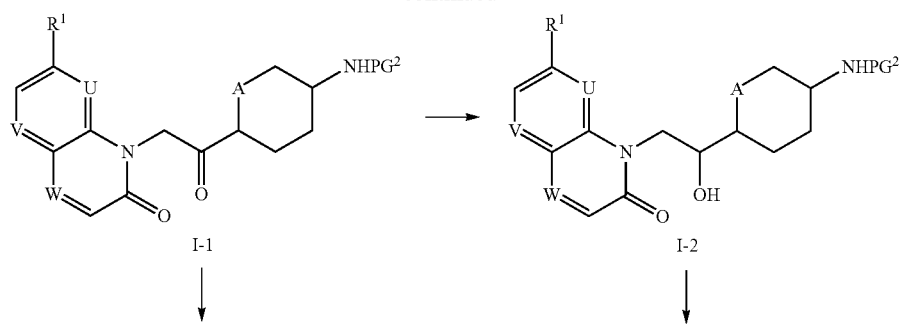
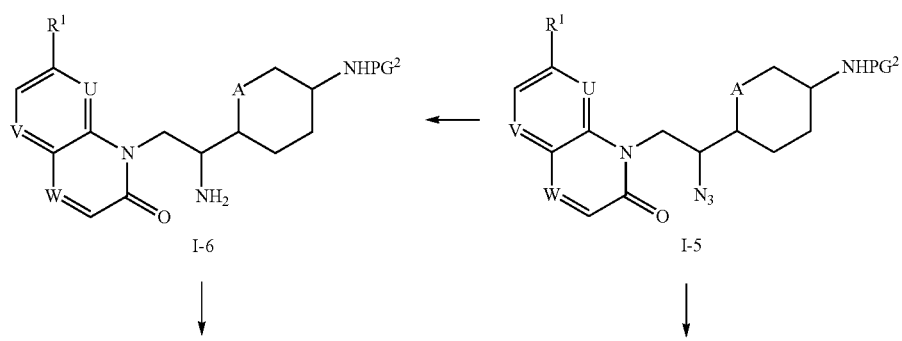
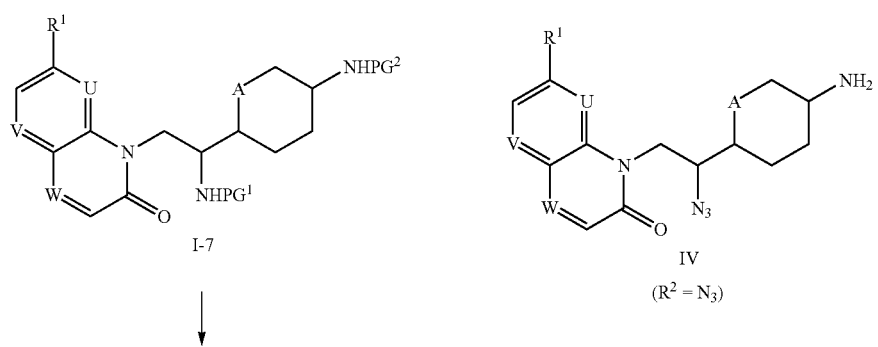
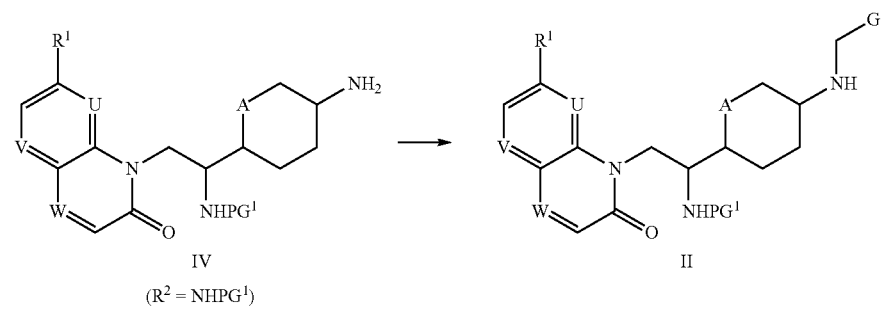

In Scheme 1, PG¹ and PG² represent independently from each other orthogonal amino protecting groups such as Cbz, Fmoc or Boc (especially PG¹=Fmoc and PG²=Boc).

The ketone derivatives of formula I-1 can be reduced using general reaction technique 6. Alternatively, the alcohols of formula I-2 can also be obtained by reaction of the derivatives of formula I-3 with the epoxides of formula I-4 in presence of an inorganic base such as K₂CO₃. The alcohols of formula I-2 can be further transformed into the corresponding azides derivatives of formula I-5 after activation of the hydroxy group using general reaction technique 7 followed by reaction with sodium azide in a solvent such as THF or DMF between 50° C. and 120° C. Alternatively, the compounds of formula I-5 can be obtained by reaction of the alcohols of formula I-2 with HN₃ or DPPA following general reaction technique 3. The amines of formula I-6 can be obtained from the azides of formula I-5 following general reaction technique 8. Alternatively, the amines of formula I-6 can be obtained by reductive amination of the ketone of formula I-1 following general reaction technique 2. The intermediates of formula I-6 can further be protected using general reaction technique 1 before sequential transformation into derivatives of formula IV wherein R² is NHPG¹ following general reaction technique 5 and into derivatives of formula II following general reaction technique 2. The compounds of formula IV wherein R² is N₃ can then be obtained by removal of the amino protecting group of the compounds of formula I-5 following general reaction technique 5.

The compounds of formula III can be obtained by reductive amination of derivatives of formula IV wherein R² is N₃ with compounds of formula G-CHO using general reaction technique 2.

The compounds of formulae I-1 and V can be prepared as described in Scheme 2 hereafter.

In Scheme 2, X represents a halogen such as bromine, PG² represents an amino protecting group such as Boc, Cbz or Fmoc and PG³ represents H or an amino protecting group such as Boc, Cbz or Fmoc.

The intermediates of formula I-3 can be reacted with the halogeno ketones of formulae II-1 and II-2 in the presence of a base such as K₂CO₃ in a solvent such as TRF or DMF between 40° C. and 100° C. to yield respectively the compounds of formulae I-1 and V.

Preparation of the Starting Compounds:

The compounds of formula I-3 wherein R¹ is MeO are either commercial (U=W=CH) or can be prepared according to literature (U=CH, W=N: WO 2008/009700; U=N, W=CH: *J. Heterocyclic Chem.* (1986), 23(2), 501-504; U=V=N: WO 2006/134378).

The compounds of formula I-3 wherein R¹ is halogen are either commercial (R¹=F, U=CH and W=CH; R¹=Br, U=CH and W=CH or W=N) or can be prepared according to literature (R¹=F, U=CH and W=N: WO 2008/009700).

The compounds of formula I-4 can be prepared as described in Scheme 3 hereafter.

Scheme 3

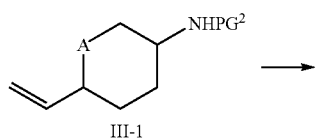

III-1

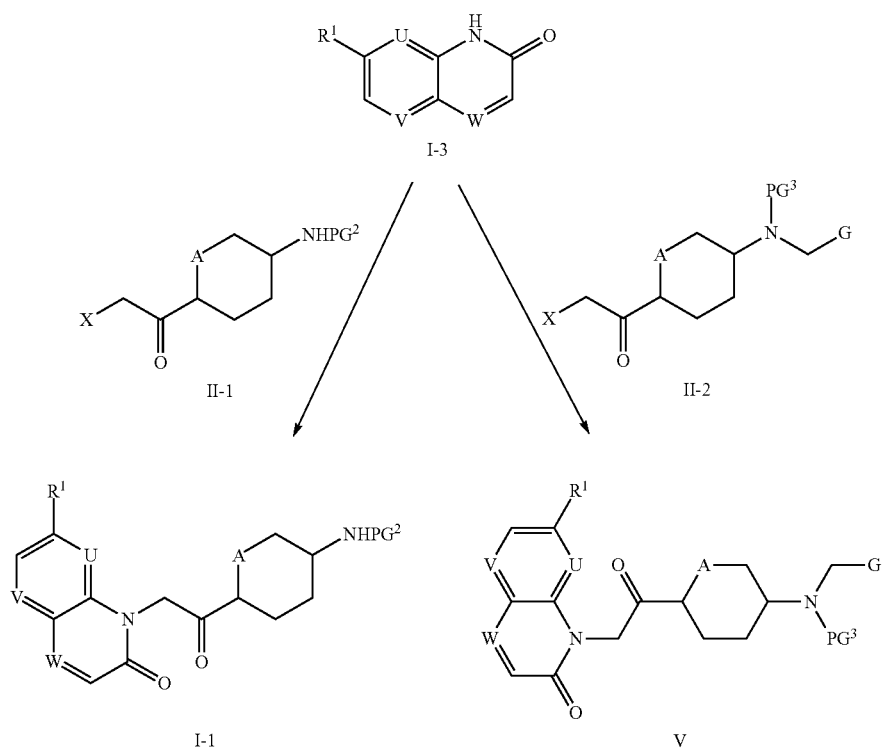

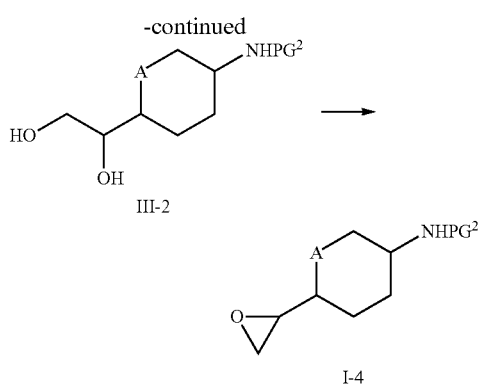

The ethylenic derivatives of formula III-1 (commercial e.g. when A=CH$_2$ and PG$^2$=Boc or prepared according WO 2006/032466 e.g. A=O and PG$^2$=Boc) can be subjected to cis-dihydroxylation using general reaction technique 9. The resulting diols of formula III-2 can be transformed into the corresponding epoxides of formula I-4 either after activation of the primary alcohol using general reaction technique 7 followed by epoxide formation in the presence of a base such as K$_2$CO$_3$ or through reaction with trimethylorthoacetate followed by reaction with TMSCl and epoxide formation in the presence of a base such as NaH. Alternatively, the epoxides can be obtained directly through epoxidation of the ethylenic derivatives of formula III-2 with a peracid such as MCPBA. In case chiral epoxides are required, they can be obtained by hydrolytic kinetic resolution (HKR) catalyzed by chiral (salen)-Co(III) complex (e.g. [(R,R)—N,N'-bis(3,5-di-tert-butylsalicylidene)-1,2-cyclohexanediaminato(2-)]cobalt(III) complex) of the racemic mixture of epoxides as described by Jacobsen et al. in *J. Am. Chem. Soc.* (2002), 124, 1307-1315 and *Science* (1997), 277, 936-938. Alternatively, the chiral epoxides can also be obtained through either Shi chiral epoxidation using a chiral ketone as described *Acc. Chem Res.* (2004), 37, 488-496 or through chiral cis-dihydroxylation using AD-mixtures following general reaction technique 9 before formation of the mesylate of the primary alcohol using general reaction technique 7 and epoxide formation under basic conditions.

The compounds of formula II-1 wherein A is CH$_2$ and PG$^2$ is Boc or Cbz are commercially available. The other compounds of formula II-1 and the compounds of formula II-2 can be prepared for example as described in Scheme 4 hereafter.

Scheme 4

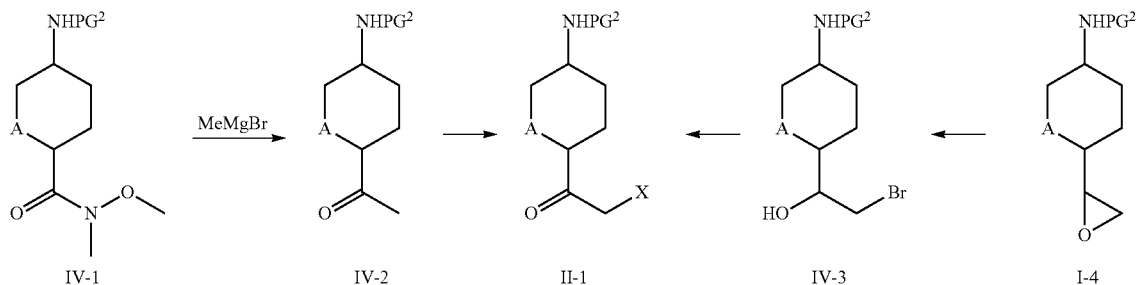

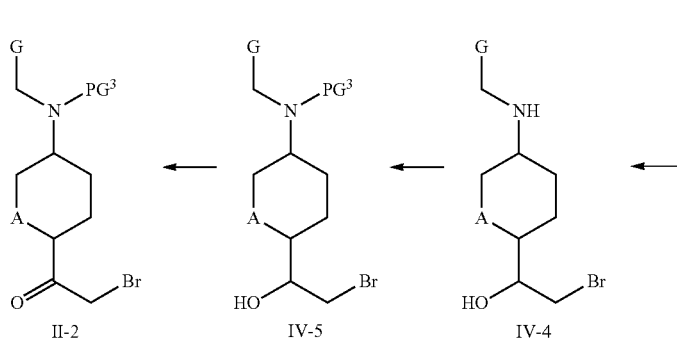

PG$^2$ = Boc

In Scheme 4, X represents a halogen such as bromine, PG$^2$ and PG$^3$ represent independently from each other amino protecting groups such as Cbz, Fmoc or Boc.

The compounds of formula II-1 can be obtained by reaction of the hydroxamate derivatives of formula IV-1 (commercially available when A=CH$_2$ or prepared from 5-(tert-butoxycarbonylamino)tetrahydropyran-2-carboxylic acid (see WO 06/032466) and N,O-dimethyl hydroxylamine in presence of propanephosphonic acid anhydride and an organic base such as DIPEA with methylmagnesium bromide. The ketones of formula IV-2 can be reacted with LiH-DMS and PTT, affording the bromoketone derivatives of formula II-1. These derivatives can also be obtained by opening the epoxides of formula I-4 with LiBr followed by oxidation of the corresponding bromoalcohol derivatives of formula IV-3 using general reaction technique 10. The compounds of formula II-2 can be obtained by removal of the protecting group of compounds of formula IV-3 followed by reductive amination with compounds of formula G-CHO using general reaction technique 2. The intermediates of formula IV-4 can be protected using general reaction technique 1, affording the intermediates of formula IV-5, which can then be oxidized into the compounds of formula 11-2 using general reaction technique 4.

Particular embodiments of the invention are described in the following Examples, which serve to illustrate the invention in more detail without limiting its scope in any way.

EXAMPLES

Preparation A: (3R,6S)-[6((2S)-oxiranyl)-tetrahydro-pyran-3-yl]-carbamic acid tert-butyl ester A. i. (3R,6S)-{6-[(2R)-1,2-dihydroxy-ethyl]-tetrahydro-pyran-3-yl}-carbamic acid tert-butyl ester (3R,6S)-(6-vinyl-tetrahydro-pyran-3-yl)-carbamic acid tert-butyl ester (prepared as described in WO 2006/032466; 4.27 g, 18.79 mmol) was dissolved in a 2-methyl-2-propanol-water mixture (1:1, 190 mL). AD-mix α® (26.30 g) was added and the mixture was stirred at rt overnight. Sodium bisulfite (28.18 g) was added. The two layers were decanted and the aq. layer was extracted twice with EA (2×150 mL). The combined org. layers were washed with brine, dried over Na$_2$SO$_4$, filtered and concentrated under reduced pressure to afford a yellow oil. The residue was purified by CC (DCM-MeOH 19:1 then 9:1), affording the title diol as a white solid (3.92 g, 80% yield). The compound was obtained as a 6-1 mixture of diastereomers.

$^1$H NMR (CDCl$_3$), major diastereomer δ: 4.23 (br. s, 1H); 4.09 (ddd, J=2.4, 5.1, 10.5 Hz, 1H); 3.68-3.74 (m, 2H); 3.52-3.66 (m, 2H); 3.35 (ddd, J=2.4, 5.1, 11.4 Hz, 1H); 2.98 (t, J=10.8 Hz, 1H); 2.51 (br. d, J=6.0 Hz, 1H); 2.09-2.21 (m, 2H); 1.78 (m, 1H); 1.54 (m, 1H); 1.43 (s, 9H); 1.22-1.36 (m, 1H).

MS (ESI, m/z): 262.4 [M+H$^+$].

A. ii. 2,2-dimethyl-propionic acid (2R)-2-[(2S,5R)-(5-tert-butoxycarbonylamino-tetrahydro-pyran-2-yl]-2-hydroxy-ethyl ester To a solution of intermediate A.i (3.92 g, 15 mmol) and DMAP (3.67 g, 30 mmol) in DCM (75 mL), cooled to 0° C., was added Piv-Cl (2.4 mL, 19.5 mmol). The reaction proceeded for 1 h. The reaction mixture was partitioned between sat. NaHCO$_3$ (100 mL) and EA (150 mL). The aq. layer was extracted with EA (100 mL). The combined org. layers were washed with brine, dried over Na$_2$SO$_4$, filtered and concentrated to dryness. The residue was purified by CC (Hept-EA 1:1) affording the title compound as a white solid (3.68 g, 71% yield).

MS (ESI, m/z): 346.1 [M+H$^+$].

A. iii. 2,2-dimethyl-propionic acid (2R)-2-[(2S,5R)-5-tert-butoxycarbonylamino-tetrahydro-pyran-2-yl]-2-methanesulfonyloxy-ethyl ester To a solution of intermediate A.ii (3.68 g, 10.653 mmol) in DCM (55 mL), cooled to 0° C. were added TEA (3.00 mL, 2 eq.) and MsCl (1.0 mL, 1.2 eq.). The reaction was stirred at 0° C. for 1 h. Sat. NaHCO$_3$ (185 mL) and DCM (185 mL) were added. The two layers were decanted and the org. layer was dried over Na$_2$SO$_4$, filtered and concentrated to dryness. The residue was purified by CC (EA-Hept 1:1), affording the title compound as a colourless foam (4.23 g, 94% yield).

MS (ESI, m/z): 424.3 [M+H$^+$].

A. iv. (3R,6S)-[6-((2S)-oxiranyl)-tetrahydro-pyran-3-yl]-carbamic acid tert-butyl ester To a solution of intermediate A.iii (4.12 g, 9.73 mmol) in THF (50 mL) was added NaOMe (25 wt % solution in MeOH, 4.5 mL). The mixture was stirred at rt for 15 min. The reaction mixture was partitioned between 10% aq. NaHSO$_4$ (100 mL) and EA (200 mL). The org. layer was dried over Na$_2$SO$_4$, filtered and concentrated under reduced pressure then dried under HV to afford the title epoxide as a pale yellow solid (2.36 g, quant.). The compound was obtained as a 6:1 mixture of diastereomers.

$^1$H NMR (CDCl$_3$) δ: 4.22 (br. s, 1H); 4.11 (m, 1H); 3.60 (br. s, 1H); 2.92-3.11 (m, 3H); 2.78 (m, 1H); 2.64 (m, 1H); 2.11 (m, 1H); 1.54-1.78 (m, 2H); 1.43 (s, 9H); 1.27 (qd, J=4.2, 12.3 Hz, 1H).

MS (ESI, m/z): 244.3 [M+H$^+$].

Preparation B:
trans-[4-(2-bromo-acetyl)-cyclohexyl]-carbamic acid tert-butyl ester B.i. (4-acetyl-cyclohexyl)-carbamic acid tert-butyl ester To a solution of [4-(methoxy-methyl-carbamoyl)-cyclohexyl]-carbamic acid tert-butyl ester (11 g, 38.4 mmol) in ether (200 mL), cooled to 0° C., was added MeMgBr (3M in ether, 32 mL, 96 mmol). The mixture was stirred 4 h at rt. 10% aq. NaHSO$_4$ (200 mL) was carefully added. The two layers were decanted and the aq. layer was extracted with EA (100 mL). The combined org. layers were washed with brine, dried over Na$_2$SO$_4$, filtered and concentrated to dryness. The residue was purified by CC (Hept-EA 2:1), affording the title methyl ketone as a white solid (7.4 g, 80% yield).

$^1$H NMR (d$_6$DMSO) δ: 6.69 (br. d, J=7.2 Hz, 1H); 3.10 (m, 1H); 2.22 (m, 1H); 2.06 (s, 3H); 1.74-1.88 (m, 4H); 1.36 (s, 9H); 1.06-1.26 (m, 4H).

B.ii. trans-[4-(2-bromo-acetyl)-cyclohexyl]-carbamic acid tert-butyl ester

To a solution of LiHMDS (1M in THF, 55 mL) cooled to -78° C., was added dropwise TMSCl (33 mL, 260 mmol). After 5 min, a solution of intermediate B.i (5.7 g, 23.62 mmol) in THF (100 mL) was added dropwise. The mixture was stirred 25 min at this temperature before quick warming to 0° C. After 10 min, PTT (9.76 g, 25.95 mmol) was added in one portion and the mixture was stirred at 0° C. for 35 min. The reaction mixture was poured into sat. NaHCO$_3$ (200 mL) and diluted with EA (100 mL). The org. layer was washed with brine, dried over Na$_2$SO$_4$, filtered and concentrated to dryness. The residue was triturated in EA-Hept, filtered and dried under HV to afford the title compound as a yellowish solid (5.3 g).
$^1$H NMR (CDl$_3$) δ: 4.36 (br. s, 1H); 4.12 (s, 1H); 3.92 (s, 1H); 3.38 (br. s, 1H); 2.63 (m, 1H); 2.04-2.16 (m, 2H); 1.88-2.00 (m, 2H); 1.41-1.50 (m, 2H); 1.43 (s, 9H), 1.08-1.22 (m, 2H).

Reference Example 1 rac-6-(trans-{4-[1-amino-2-(7-methoxy-2-oxo-2H-quinolin-1-yl)-ethyl]-cyclohexylamino}-methyl)-4H-pyrido[3,2-b][1,4]thiazin-3-one R1.i. rac-{trans-4-[2-(7-methoxy-2-oxo-2H-quinolin-1-yl)-acetyl]-cyclohexyl}-carbamic acid tert-butyl ester To a mixture of the compound of preparation B (3.20 g, 10 mmol) and 7-methoxy-1H-quinolin-2-one (1.46 g, 7.5 mmol) in DMF (40 mL) was added K$_2$CO$_3$ (2.07 g, 15 mmol). The mixture was heated at 75° C. for 45 min. The solvent was evaporated in vacuo and the residue was partitioned between water (100 mL) and EA (200 mL). The org. layer was dried over Na$_2$SO$_4$, filtered and concentrated to dryness. The residue was chromatographed (Hept-EA 1-1 then 4-1) to afford the title compound as a white solid (1.7 g, 55% yield).
$^1$H NMR (d$_6$DMSO) δ: 7.86 (d, J=9.3 Hz, 1H); 7.64 (d, J=8.7 Hz, 1H); 6.87 (dd, J=2.4, 8.7 Hz, 1H); 6.75 (d, J=8.1 Hz, 1H); 6.64 (d, J=2.4 Hz, 1H); 6.41 (d, J=9.3 Hz, 1H); 5.31 (s, 2H); 3.82 (s, 3H); 3.19 (br. s, 1H); 2.64 (m, 1H); 2.00 (m, 2H); 1.88 (m, 2H); 1.18-1.41 (m, 4H); 1.39 (s, 9H).
MS (ESI, m/z): 415.2 [M+H$^+$].

R1.ii. rac-{trans-4-[hydroxy-(7-methoxy-2-oxo-2H-quinolin-1-yl)-methyl]cyclohexyl}-carbamic acid tert-butyl ester To a mixture of intermediate R1.i (1.7 g, 4.1 mmol) in MeOH (30 mL) and TRF (3 mL) was added NaBH$_4$ (0.775 g, 20 mmol). The mixture was stirred at the same temperature for 1 h. Water (200 mL) was added. The volatiles were removed in vacuo. The residue was taken up in EA (200 mL). The two layers were decanted and the org. layer was dried over Na$_2$SO$_4$, filtered and concentrated to dryness. The residue was dried under HV to afford the title alcohol as a yellowish foam (1.7 g, 100% yield).
MS (ESI, m/z): 417.4 [M+H$^+$].

R1.iii. rac-1-[trans-2-(4-amino-cyclohexyl)-2-hydroxy-ethyl]-7-methoxy-1H-quinolin-2-one A solution of intermediate R1.ii (1.7 g, 4.1 mmol) in TFA (10 mL) and DCM (2 mL) was stirred at rt for 20 min. The solvents were removed in vacuo and the residue was partitioned between sat. NaHCO$_3$ (20 mL) and 1M NaOH (20 mL). The aq. layer was extracted with DCM-MeOH (9-1, 5×150 mL). The combined org. layers were washed with brine (20 mL), dried over Na$_2$SO$_4$, filtered and concentrated to dryness. After CC (DCM-MeOH 9-1 containing 1% v/v aq. NH$_4$OH), the title amine was obtained as a yellowish foam (0.92 g, 71% yield).
$^1$H NMR (CDCl$_3$) δ: 7.65 (d, J=9.3 Hz, 1H); 7.49 (d, J=8.7 Hz, 1H); 6.84 (dd, J=2.4, 8.7 Hz, 1H); 6.80 (d, J=2.4 Hz, 1H); 6.56 (d, J=9.3 Hz, 1H); 4.65 (dd, J=9.9, 14.7 Hz, 1H); 4.12 (dd, J=2.1, 14.7 Hz, 1H); 3.90 (s, 3H); 3.86 (overlapped ddd, J=2.4, 5.7, 9.9 Hz, 1H); 2.67 (tt, J=3.9, 10.8 Hz, 1H); 1.88-2.10 (m, 5H); 1.64-1.09 (m, 7H).
MS (ESI, m/z): 317.4 [M+H$^+$].

R1.iv. trans-{4-[(1RS)-1-hydroxy-2-(7-methoxy-2-oxo-2H-quinolin-1-yl)-ethyl]-cyclohexyl}-carbamic acid benzyl ester To a solution of intermediate R1.iii (0.82 g, 2.6 mmol) in acetone (10 mL) and water (5 mL), cooled to 0° C., were added NaHCO$_3$ (0.435 g, 5.2 mmol) and Cbz-Cl (0.45 mL, 3.12 mmol). The reaction mixture was stirred at 0° C. for 1 h before warming to rt. After 1 h, the reaction mixture was diluted with water (100 mL), and the solids were filtered off. The solids were thoroughly washed with water and taken up in EA (200 mL). The org. layer was washed with brine, dried over Na$_2$SO$_4$, filtered and concentrated to dryness to afford the title compound as a white solid (1.14 g, 98% yield).
MS (ESI, m/z): 451.4 [M+H$^+$].

R1.v. rac-methanesulfonic acid trans-1-(4-benzyloxycarbonylamino-cyclohexyl)-2-(7-methoxy-2-oxo-2H-quinolin-1-yl)-ethyl ester To a solution of intermediate R1.iv (1.18 g, 2.64 mmol) in DCM (30 mL) were added TEA (0.735 mL, 5.28 mmol) and MsCl (0.245 mL, 3.17 mmol). The reaction was stirred at the same temperature for 30 min. The reaction mixture was partitioned between sat. NaHCO$_3$ (30 mL) and DCM (100 mL). The org. layer was dried over Na$_2$SO$_4$, filtered and concentrated to dryness, affording the title mesylate as a colourless foam (1.40 g, quant.).
MS (ESI, m/z): 529.3 [M+H$^+$].

R1.vi. rac-{trans-4-[1-azido-2-(7-methoxy-2-oxo-2H-quinolin-1-yl)-ethyl]-cyclohexyl}-carbamic acid benzyl ester To a solution of intermediate R1.v (1.40 g, 2.64 mmol) in DMF (15 mL) was added NaN$_3$ (0.516 g, 7.94 mmol). The mixture was heated 80° C. for 2 h. The reaction mixture was cooled to rt and diluted with water (100 mL). The solids were filtered off and taken up in EA (300 mL). The org. layer was washed with brine, dried over Na$_2$SO$_4$, filtered and concentrated to dryness to afford the title azide as a colourless foam (1.14 g, 91% yield).
MS (ESI, m/z): 476.2 [M+H$^+$].

R1.vii. rac{trans-4-[1-amino-2-(7-methoxy-2-oxo-2H-quinolin-1-yl)-ethyl]-cyclohexyl}-carbamic acid benzyl ester To a solution of intermediate R1.vi (1.14 g, 2.41 mmol) in TRF (12 mL) and water (3 mL) was added PPh$_3$ (1.29 g, 4.85 mmol). The mixture was stirred at 55° C. for 8 h. After cooling to rt, the solvent was evaporated to dryness and the residue was directly purified by CC (DCM-MeOH 9:1 containing 1% v/v aq. NH$_4$OH), affording the title compound as a colourless foam (0.950 g, 87% yield).
$^1$H NMR (CDCl$_3$) δ: 7.59 (d, J=9.3 Hz, 1H); 7.47 (d, J=9.0 Hz, 1H); 7.30-7.38 (m, 5H); 6.80-6.83 (m, 2H); 6.55 (d, J=9.3 Hz, 1H); 5.09 (s, 2H); 4.60 (overlapped br. s, 1H); 4.56 (dd, J=9.9, 14.1 Hz, 1H); 4.06 (dd, J=4.2, 14.1 Hz, 1H); 3.90 (s, 3H); 3.48 (m, 1H); 3.09 (m, 1H); 2.04-2.18 (m, 3H); 1.87 (m, 1H); 1.10-1.50 (m, 7H).
MS (ESI, m/z): 450.3 [M+H$^+$].

R1.viii. trans-{4-[(1RS)-1-tert-butoxycarbony-lamino-2-(7-methoxy-2-oxo-2H-quinolin-1-yl)-ethyl]-cyclohexyl}-carbamic acid benzyl ester To a solution of intermediate R1.vii (0.95 g, 2.11 mmol) in DCM (10 mL) was added Boc$_2$O (0.7 g, 3.2 mmol). The mixture was stirred at rt overnight. The solvent was evaporated to dryness and the residue was triturated in Hept and DIPE to afford the title compound as a white solid (1.2 g, quant.).
MS (ESI, m/z): 550.2 [M+H$^+$].

R1.ix. rac-[trans-1-(4-amino-cyclohexyl)-2-(7-methoxy-2-oxo-2H-quinolin-1-yl)-ethyl]-carbamic acid tert-butyl ester To a solution of intermediate R1.viii (1.2 g, 2.11 mmol) in EA (20 mL) was added 20% Pd(OH)$_2$/C (moisturized, 0.6 g). The reaction mixture was stirred under hydrogen atmosphere for 3 h. The catalyst was removed by filtration and the filtrate was concentrated to dryness. The residue was purified by CC (DCM-MeOH 9:1 containing 1% v/v aq. NH$_4$OH) to afford the title amine as a white foam (0.7 g, 77% yield).
MS (ESI, m/z): 416.3 [M+H$^+$].

R1.x. rac-(2-(7-methoxy-2-oxo-2H-quinolin-1-yl)-1-trans-{4-[(3-oxo-3,4-dihydro-2H-pyrido[3,2-b][1,4]thiazin-6-ylmethyl)-amino]-cyclohexyl}-ethyl)-carbamic acid tert-butyl ester To a solution of intermediate R1.ix (0.2 g, 0.481 mmol) in DCE (9 mL) and MeOH (3 mL) were added 3 Å molecular sieves (2.0 g) and 3-oxo-3,4-dihydro-2H-pyrido[3,2-b][1,4]thiazine-6-carbaldehyde (prepared according to WO 02/056882; 0.098 g, 1.05 eq.). The mixture was stirred overnight at 50° C. After cooling, NaBH$_4$ (0.16 g) was added. The reaction proceeded 45 min. The reaction mixture was diluted with DCM-MeOH (9-1, 100 mL). The solids were filtered off and washed with DCM (50 mL). The filtrate was washed with sat. NaHCO$_3$ (50 mL), dried over Na$_2$SO$_4$, filtered and concentrated to dryness. After CC (DCM-MeOH 9-1 containing 1% v/v aq. NH$_4$OH), the title compound was obtained as a beige solid (0.28 g, 98% yield).
MS (ESI, m/z): 594.2 [M+H$^+$].

R1.xi. rac-6-(trans-{4-[1-amino-2-(7-methoxy-2-oxo-2H-quinolin-1-yl)-ethyl]-cyclohexylamino}-methyl)-4H-pyrido[3,2-b][1,4]thiazin-3-one Starting from intermediate R1.x (0.280 g, 0.47 mmol), the title compound was obtained as a beige solid (0.2 g, 86% yield) using the procedure of step R1.iii. The crude material was triturated in ether.
$^1$H NMR (d$_6$DMSO) δ: 10.82 (br. s, 1H); 7.79 (d, J=9.3 Hz, 1H); 7.70 (d, J=7.8 Hz, 1H); 7.60 (d, J=8.4 Hz, 1H); 7.07 (d, J=7.8 Hz, 1H); 6.93 (d, J=2.1 Hz, 1H); 6.86 (dd, J=2.1, 8.4 Hz, 1H); 6.39 (d, J=9.3 Hz, 1H); 4.18 (br. d, J=6.3 Hz, 2H); 3.85 (s, 3H); 3.71 (s, 2H); 3.50 (s, 2H); 2.89 (m, 1H); 2.29 (m, 1H); 1.84-2.00 (m, 3H); 1.50-1.80 (m, 3H); 0.93-1.30 (m, 6H).
MS (ESI, m/z): 494.2 [M+H$^+$].

Reference Example 2 rac-6-(trans-{4-[1-amino-2-(7-methoxy-2-oxo-2H-quinolin-1-yl)-ethyl]-cyclohexylamino}-methyl)-4H-pyrido[3,2-b][1,4]oxazin-3-one Starting from intermediate R1.ix (0.2 g, 0.481 mmol) and 3-oxo-3,4-dihydro-2H-pyrido[3,2-b][1,4]oxazine-6-carbaldehyde (prepared according to WO 02/056882; 0.095 g, 1.1 eq.), the title compound was obtained as a white solid (0.160 g) using sequentially the procedures of Reference Example 1, steps R1.x and R1.iii (reductive amination, 79% yield; Boc deprotection, 88% yield). The crude materials were purified by CC using DCM-MeOH 9:1 containing 1% v/v aq. NH$_4$OH as eluent if necessary.
$^1$H NMR (d$_6$DMSO) δ: 7.79 (d, J=9.3 Hz, 1H); 7.61 (d, J=8.7 Hz, 1H); 7.27 (d, J=7.8 Hz, 1H); 7.00 (d, J=7.8 Hz, 1H); 6.93 (d, J=2.4 Hz, 1H); 6.86 (dd, J=2.4, 8.7 Hz, 1H); 6.39 (d, J=9.3 Hz, 1H); 4.58 (s, 2H); 4.18 (br. d, J=6.3 Hz, 2H); 3.85 (s, 3H); 3.68 (s, 2H); 2.89 (m, 1H); 2.29 (m, 1H); 1.84-2.00 (m, 3H); 1.50-1.80 (m, 3H); 0.91-1.30 (m, 6H).
MS (ESI, m/z): 478.2 [M+H$^+$].

Example 1

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]thiazin-3-one Method A:
The compound of Reference Example 1 may be separated using chiral HPLC, affording the title compound.
Method B:

1.B.i. Trans-(4-vinyl-cyclohexyl)-carbamic acid tert-butyl ester tBuOK (13.78 g, 122.7 mmol) was added in one portion to a white suspension of methyl triphenylphosphonium bromide (43.85 g, 122.7 mmol) in THF (145 mL) at rt under nitrogen. The resulting suspension was stirred for 1 h at rt and a solution of trans-(4-formyl-cyclohexyl)-carbamic acid tert-butyl ester (13.95 g, 61.37 mmol) in THF (40 mL) was added. The mixture was stirred 30 min at rt. A 10% NaHSO$_4$ solution (240 mL) was added and the mixture was diluted with EA (500 mL). The two layers were decanted and the aq. layer was extracted once with EA (250 mL). The combined org. layers were washed with brine, dried over Na$_2$SO$_4$, filtered and concentrated to dryness. The residue was quickly filtered (EA-Hept 1-2) to afford the title compound as a white solid (13.58 g).
MS (ESI, m/z): 226.2 [M+H$^+$].

1.B.ii. [4-((2R)-1,2-dihydroxy-ethyl)-cyclohexyl]-carbamic acid tert-butyl ester To a mixture of the intermediate 1.B.i (21.65 g, 96.08 mmol) in 2-methyl-2-propanol (480 mL) and water (480 mL) were added potassium ferricyanide (94.9 g), potassium carbonate (39.9 g), (DHQD)$_2$Pyr (0.847 g) and K$_2$OsO$_2$(OH)$_2$ (0.354 g). The mixture was stirred at 0° C. for 30 h. The reaction was then carefully quenched with sodium bisulfite (144 g). The two layers were then decanted and the aq. layer was extracted once with EA (400 mL). The combined org. layers were dried over Na$_2$SO$_4$, filtered and concentrated to dryness. The resulting oil was purified by CC (DCM-MeOH 9-1) to afford the title compound as a yellow solid (23.02 g, 92% yield).
MS (ESI, m/z): 260.2 [M+H$^+$].

1.B.iii. Trans-[4-((2S)-oxiranyl)-cyclohexyl]-carbamic acid tert-butyl ester To a solution of the intermediate 1.B.ii (23.02 g, 88.762 mmol) in DCM (240 mL) was added TsOH (0.795 g, 0.05 eq.)

followed by trimethyl orthoacetate (16.1 mL, 1.3 eq.). The reaction proceeded at rt for 30 min. The solvents were removed under reduced pressure and the residue was further dried under HV for 10 min. The residue was taken up in DCM (120 mL) and MeOH (0.03 mL) and TMSCl (16.0 mL, 1.4 eq.) was added. The reaction mixture was then stirred at rt for 1 h. A sat. aq. NaHCO$_3$ solution (250 mL) was added and the two layers were separated. The org. layer was dried over Na$_2$SO$_4$, filtered and concentrated to dryness. The residue was taken up in MeOH (150 mL) and NaOMe (25% wt in MeOH, 40.5 mL) was added. The reaction proceeded at rt for 1 h. The reaction mixture was diluted with DCM (300 mL) and a 10% NaHSO$_4$ solution (120 mL). The aq. layer was extracted three times with DCM-MeOH 9-1 (3 x 150 mL). The combined org. layers were washed with brine (200 mL), dried over Na$_2$SO$_4$, filtered and concentrated to give a yellow oil. The residue was chromatographed (EA/Hept 2:1) to afford the title compound as a white solid (17.35 g).

MS (ESI, m/z): 260.2 [M+H$^+$].

1.B.iv. 1-[(2R)-2-(4-aAmino-cyclohexyl)-2-azido-ethyl]-7-methoxy-1H-quinolin-2-one Starting from the intermediate 1.B.iii (1.3 g, 5.38 mmol) and 7-methoxy-1H-quinolin-2-one (0.97 g, 5.51 mmol), the title compound (0.396 g) was prepared as a yellowish foam using the procedures described in Example 3, steps 3.i (epoxide opening, 50% yield), 3.ii (mesylate formation, 98% yield), 3.iii (azide formation, 72% yield) and 3.iv (Boc removal, 100% yield). If necessary, the crude reaction mixtures were purified by chromatography using an appropriate eluent.

MS (ESI, m/z): 342.4 [M+H$^+$].

1.B.v. 6-(trans-{4-[(1R)-1-amino-2-(7-methoxy-2-oxo-2H-quinolin-1-yl)-ethyl]-cyclohexylamino}-methyl)-4H-pyrido[3,2-b][1,4]-thiazin-3-one Starting from intermediate 1.B.iv (0.090 g, 0.262 mmol) and 3-oxo-3,4-dihydro-2H-pyrido[3,2-b][1,4]thiazine-6-carbaldehyde (0.051 g, 1 eq.), the title compound was obtained as a off-white foam (0.094 g) using the procedures of Reference Example 1, step R1.x (reductive amination, 82% yield) and Example 3, step 3.vi (Staudinger reduction, 98% yield). The crude materials were purified by CC using a gradient of DCM-MeOH containing 10% aq. NH$_4$OH as eluent.

MS (ESI, m/z): 494.3 [M+H$^+$].

Example 2

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]oxazin-3-one Method A:
The compound of Reference Example 2 may be separated using chiral HPLC, affording the title compound.
Method B:
Starting from intermediate 1.B.iv (0.100 g, 0.293 mmol) and 3-oxo-3,4-dihydro-2H-pyrido[3,2-b][1,4]oxazine-6-carbaldehyde (0.053 g, 1 eq.), the title compound was obtained as a white solid (0.089 g) using the procedures of Reference Example 1, step R1.x (reductive amination, 75% yield) and Example 3, step 3.vi (Staudinger reduction, 98% yield). The crude materials were purified by CC using a gradient of DCM-MeOH containing 10% aq. NH$_4$OH as eluent.

MS (ESI, m/z): 478.0 [M+H$^+$].

Example 3

6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]oxazin-3-one 3.i. {6-[1-hydroxy-2-(7-methoxy-2-oxo-2H-quinolin-1-yl)-ethyl]-tetrahydro-pyran-3-yl}-carbamic acid tert-butyl ester To a solution of the compound of preparation A (1.040 g, 4.275 mmol) in DMF (5.5 mL) was added a suspension of 7-methoxy-1H-quinolin-2-one (0.824 g, 1.1 eq.) in DMF (11 mL) and Cs$_2$CO$_3$ (2.78 g, 2 eq.). The reaction mixture was stirred at 80° C. for 5 h. The solvent was removed under reduced pressure, then the residue was partitioned between water (100 mL) and EA (100 mL). The aq. layer was extracted once more with EA (100 mL). The org. layer was dried over Na$_2$SO$_4$, filtered and evaporated to dryness. The residue was purified by CC (EA-Hept 4-1) to afford the title compound as a yellow foam (0.784 g, 44% yield).

MS (ESI, m/z): 419.3 [M+H$^+$].

3.ii. Methanesulfonic acid (1S)-1-((2S,5R)-5-tert-butoxycarbonylamino-tetrahydro-pyran-2-yl)-2-(7-methoxy-2-oxo-2H-quinolin-1-yl)-ethyl ester To a solution of intermediate 3.i (0.770 g, 1.840 mmol) in DCM (10 mL), cooled to 0° C. were added TEA (0.52 mL, 2 eq.) and Ms-Cl (0.18 mL, 1.2 eq.). The reaction was stirred at 0° C. for 1 h. Sat. NaHCO$_3$ (30 mL) and DCM (30 mL) were added. The two layers were decanted and the org. layer was dried over Na$_2$SO$_4$, filtered and concentrated to dryness. The residue was purified by CC (EA-Hept 2:1) to afford the title compound as a white solid (0.545 g, 60% yield). The compound was obtained as a 6:1 mixture of diastereomers.

$^1$H NMR (CDCl$_3$), major diastereomer δ: 7.62 (d, J=9.3 Hz, 1H); 7.45 (d, J=8.7 Hz, 1H); 7.04 (d, J=2.1 Hz, 1H); 6.83 (dd, J=2.1, 8.7 Hz, 1H); 6.51 (d, J=9.3 Hz, 1H); 5.04 (m, 1H); 4.75 (m, 1H); 4.50 (m, 1H); 4.14-4.28 (m, 2H); 3.91 (s, 3H); 3.51 (m, 1H); 3.46 (dd, J=5.1, 12.6 Hz, 1H); 3.04 (t, J=10.5 Hz, 1H); 2.76 (s, 3H); 2.17 (m, 1H); 1.71-1.90 (m, 2H); 1.44 (s, 9H); 1.31 (m, 1H).

MS (ESI, m/z): 497.4 [M+H$^+$].

3.iii. {(3R,6S)-6-[(1S)-1-azido-2-(7-methoxy-2-oxo-2H-quinolin-1-yl)-ethyl]-tetrahydro-pyran-3-yl}-carbamic acid tert-butyl ester A 6:1 mixture of intermediate 3.ii and its diasteromer (0.545 g, 1.091 mmol) and NaN$_3$ (0.192 g, 2.7 eq.) in DMF (9 mL) were heated at 80° C. for 45 min. The solvent was removed under HV and the residue was partitioned between water (70 mL) and EA (80 mL). The aq. layer was extracted once with EA (70 mL). The combined org. layers were washed with brine, dried over Na$_2$SO$_4$, filtered and concentrated to dryness. The residue was purified by CC (EA-Hept 2:1) to afford the title azide as a white foam (0.484 g, 100% yield). The compound was obtained as a 6:1 mixture of diastereomers.

$^1$H NMR (CDCl$_3$) major diastereomer δ: 7.63 (d, J=9.3 Hz, 1H); 7.46 (d, J=8.7 Hz, 1H); 7.07 (d, J=2.4 Hz, 1H); 6.83 (dd, J=2.4, 8.7 Hz, 1H); 6.52 (d, J=9.3 Hz, 1H); 4.53 (dd, J=7.8, 14.1 Hz, 1H); 4.43 (dd, J=5.1, 14.1 Hz, 1H); 4.16-4.24 (m, 2H); 3.91 (s, 3H); 3.84 (m, 1H); 3.67 (m, 1H); 3.42 (m, 1H); 2.97 (t, J=10.5 Hz, 1H); 2.17 (m, 1H); 1.74-1.92 (m, 2H); 1.44 (s, 9H); 1.31 (m, 1H).
MS (ESI, m/z): 444.0 [M+H$^+$].

3.iv. 1-[(2S)-2-((2S,5R)-5-amino-tetrahydro-pyran-2-yl)-2-azido-ethyl]-7-methoxy-1H-quinolin-2-one Starting from a 6:1 mixture of intermediate 3.iii and its diasteromer (0.265 g, 0.6 mmol), the title amine was obtained as a yellowish foam (0.202 g, 98% yield) using the procedure of Reference Example 1, step R1.iii. The crude material was carried on without further purification.
MS (ESI, m/z): 344.5 [M+H$^+$].

3.v. 6-({(3R,6S)-6-[(1S)-1-azido-2-(7-methoxy-2-oxo-2H-quinolin-1-yl)-ethyl]-tetrahydro-pyran-3-ylamino}-methyl)-4H-pyrido[3,2-b][1,4]oxazin-3-one Starting from the crude material obtained at step 3.iv (0.110 g, 0.173 mmol) and 3-oxo-3,4-dihydro-2H-pyrido[3,2-b][1,4]oxazine-6-carbaldehyde (0.057 g, 1 eq.), the title compound was obtained as a white solid (0.138 g, 85% yield) using the procedure of Reference Example 1, step R1.x. The crude material was purified by CC (DCM-MeOH 93:7 containing 0.7% v/v aq. NH$_4$OH).
$^1$H NMR (d$_6$DMSO) δ: 11.13 (s, 1H); 7.83 (d, J=9.6 Hz, 1H); 7.63 (d, J=8.1 Hz, 1H); 7.28 (d, J=8.7 Hz, 1H); 6.98-7.01 (m, 2H); 6.89 (dd, J=2.1, 8.7 Hz, 1H); 6.41 (d, J=9.6 Hz, 1H); 4.63 (overlapped m, 1H); 4.59 (s, 3H); 4.27 (dd, J=5.1, 15.0 Hz, 1H); 4.02 (m, 1H); 3.86 (s, 3H); 3.67-3.75 (m, 3H); 3.47 (m, 1H); 2.96 (t, J=10.5 Hz, 1H); 1.99-2.09 (m, 2H); 1.74 (m, 1H); 1.51 (m, 1H); 1.22 (m, 1H).
MS (ESI, m/z): 506.4 [M+H$^+$].

3.vi. 6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]oxazin-3-one To a solution of intermediate 3.v (0.130 g, 0.257 mmol) in THF (4 mL) was added PPh$_3$ (0.136 g, 2 eq.). The mixture was heated at 60° C. for 50 min, then water (1.2 mL) was added. After 3 h, the reaction mixture was cooled to rt and the solvents were removed in vacuo. The residue was purified by CC (DCM-MeOH 93:7 containing 0.7% aq. NH$_4$OH) to afford the title compound as an off-white solid (0.105 g, 85% yield).
$^1$H NMR (d$_6$DMSO) δ: 7.78 (d, J=9.3 Hz, 1H); 7.59 (d, J=8.7 Hz, 1H); 7.27 (d, J=8.1 Hz, 1H); 7.06 (d, J=2.1 Hz, 1H); 6.99 (d, J=8.1 Hz, 1H); 6.85 (dd, J=2.1, 8.7 Hz, 1H); 6.38 (d, J=9.3 Hz, 1H); 4.58 (s, 2H); 4.30 (m, 1H); 4.02-4.12 (m, 2H); 3.97 (m, 1H); 3.83 (s, 3H); 3.68 (dd, AB syst. J=14.7 Hz, Δ=0.06 ppm, 2H); 3.15 (d, J=4.8 Hz, 1H); 3.06 (m, 1H); 2.97 (m, 1H); 2.90 (t, J=10.5 Hz, 1H); 1.98 (m, 1H); 1.91 (br. s, 1H); 1.50-1.64 (m, 2H); 1.51 (br. s, 1H); 1.16 (m, 1H).
MS (ESI, m/z): 480.3 [M+H$^+$].

Example 4

1-((2S)-2-amino-2-{(2S,5R)-5-[(E)-3-(2,5-difluoro-phenyl)-allylamino]-tetrahydro-pyran-2-yl}-ethyl)-7-methoxy-1H-quinolin-2-one Starting from intermediate 3.iv (0.100 g, 0.291 mmol) and (E)-3-(2,5-difluoro-phenyl)-propenal (0.049 g, 1 eq.), the title compound was obtained as a yellowish foam (0.021 g) using the procedures of Reference Example 1, step R1.iv (reductive amination, 60% yield) and Example 3, step 3.vi (Staudinger reduction, 25% yield). The crude materials were purified by CC using a DCM-MeOH containing 10% aq. NH$_4$OH gradient as eluent.
$^1$H NMR (d$_6$DMSO) δ: 7.78 (d, J=9.3 Hz, 1H); 7.59 (d, J=8.7 Hz, 1H); 7.44 (m, 1H); 7.22 (m, 1H); 7.04-7.11 (m, 2H); 6.85 (dd, J=2.4, 8.4 Hz, 1H); 6.58 (d, J=16.2 Hz, 1H); 6.46 (td, J=5.4, 16.2 Hz, 1H); 6.39 (d, J=9.3 Hz, 1H); 4.31 (dd, J=8.1, 13.8 Hz, 1H); 3.98-4.11 (m, 2H); 3.83 (s, 3H); 3.36 (br. t, J=5.4 Hz, 2H); 3.07 (m, 1H); 2.99 (m, 1H); 2.90 (t, J=10.5 Hz, 1H); 2.02 (m, 1H); 1.48-1.68 (m, 5H); 1.22-1.08 (m, 2H).
MS (ESI, m/z): 470.3 [M+H$^+$].

Example 5

6-({3R,6,S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]thiazin-3-one Starting from intermediate 3.iv. (0.090 g, 0.262 mmol) and 3-oxo-3,4-dihydro-2H-pyrido[3,2-b][1,4]thiazine-6-carbaldehyde (0.051 g, 1 eq.), the title compound was obtained as a yellowish foam (0.094 g) using the procedures of Reference Example 1, step R1.x (reductive amination, 83% yield) and Example 3, step 3.vi (Staudinger reduction, 91% yield). The crude materials were purified by CC using a gradient of DCM-MeOH containing 10% aq. NH$_4$OH as eluent.
$^1$H NMR (d$_6$DMSO) δ: 10.81 (s, 1H); 7.78 (d, J=9.3 Hz, 1H); 7.71 (d, J=8.1 Hz, 1H); 7.60 (d, J=8.7 Hz, 1H); 7.06 (d, J=8.1 Hz, 1H); 7.05 (d, J=2.1 Hz, 1H); 6.85 (dd, J=2.1, 8.7 Hz, 1H); 6.38 (d, J=9.3 Hz, 1H); 4.30 (m, 1H); 4.07 (m, 1H); 3.97 (m, 1H); 3.83 (s, 3H); 3.71 (dd, AB syst., J=17.1 Hz, Δ=0.071 ppm, 2H); 3.50 (s, 2H); 3.07 (m, 1H); 2.98 (m, 1H); 2.90 (t, J=10.5 Hz, 1H); 2.01 (m+overlapped br. s, 2H); 1.41-1.60 (m, 4H); 1.10-1.25 (m, 2H).
MS (ESI, m/z): 496.4 [M+H$^+$].

Example 6

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]thiazin-3-one

6.i. {(3R,6S)-6-[(1S)-1-hydroxy-2-(7-methoxy-2-oxo-2H-[1,5]naphthyridin-1-yl)-ethyl]tetrahydro-pyran-3-yl}-carbamic acid tert-butyl ester Starting from 7-methoxy-1H-[1,5]naphthyridin-2-one (prepared according to WO 2007/138974; 2.0 g, 11.3 mmol) and the compound of Preparation A (2.50 g, 10.27 mmol), the title compound was obtained as a colourless foam (1.82 g, 42% yield) using the procedure described in Example 3, step 3.i. The crude material was purified by CC (DCM-MeOH 97:3). The compound was obtained as a 6:1 mixture of diastereomers.
MS (ESI, m/z): 420.1 [M+H$^+$].

6.ii. 1-[(2S)-2-((2S,5R)-5-amino-tetrahydro-pyran-2-yl)-2-azido-ethyl]-7-methoxy-1H-[1,5]naphthyridin-2-one Starting from intermediate 6.i (1.6 g, 3.81 mmol), the title azide was obtained as a thick yellowish oil (0.694 g, 2.01 mmol) using sequentially the procedures reported in Example 3, steps 3.ii (mesylate formation, 72% yield), 3.iii (azide formation, 81% yield) and 3.iv (Boc deprotection, 92% yield). If necessary, the crude reaction mixtures were purified by CC using a suitable eluent. The compound was obtained as a 8:1 mixture of diastereomers. (MS (ESI, m/z): 345.3 [M+H$^+$].

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]thiazin-3-one Starting from intermediate 6.ii (0.1 g, 0.29 mmol) and 3-oxo-3,4-dihydro-2H-pyrido[3,2-b][1,4]thiazine-6-carbaldehyde (0.057 g, 1 eq.), the title compound was obtained as a yellowish foam (0.099 g) using the procedures reported in Reference Example 1, step R1.x (reductive amination, 92% yield) and Example 3, step 3.vi (azide reduction, 77% yield). The crude materials were purified by CC using a gradient of DCM-MeOH containing 10% aq. NH$_4$OH as eluent.

$^1$H NMR (d$_6$DMSO) δ: 10.81 (s, 1H); 8.24 (d, J=2.1 Hz, 1H); 7.82 (d, J=9.9 Hz, 1H); 7.70 (d, J=8.1 Hz, 1H); 7.47 (d, J=2.1 Hz, 1H); 7.05 (d, J=8.1 Hz, 1H); 6.62 (d, J=9.9 Hz, 1H); 4.25 (m, 1H); 4.09 (m, 1H); 3.95 (overlapped m, 1H); 3.91 (s, 3H); 3.69 (dd, AB syst., J=15.0 Hz, Δ=0.062 ppm, 2H); 3.50 (s, 2H); 3.05 (m, 1H); 2.95 (m, 1H); 2.86 (t, J=10.5 Hz, 1H); 2.01 (br. s+overlapped m, 2H); 1.48-1.58 (m, 3H); 1.42 (br. s, 1H); 1.08-1.24 (m, 2H).

MS (ESI, m/z): 497.4 [M+H$^+$].

Example 7

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]oxazin-3-one Starting from intermediate 6.ii (0.1 g, 0.29 mmol) and 3-oxo-3,4-dihydro-2H-pyrido[3,2-b][1,4]oxazine-6-carbaldehyde (0.051 g, 1 eq.), the title compound was obtained as a white foam (0.079 g) using the procedures reported in Reference Example 1, step R1.x (reductive amination, 83% yield) and Example 3, step 3.vi (azide reduction, 69% yield). The crude materials were purified by CC using a gradient of DCM-MeOH containing 10% aq. NH$_4$OH as eluent.

$^1$H NMR (d$_6$DMSO) δ: 8.24 (d, J=2.4 Hz, 1H); 7.83 (d, J=9.6 Hz, 1H); 7.48 (d, J=2.4 Hz, 1H); 7.28 (d, J=8.1 Hz, 1H); 6.98 (d, J=8.1 Hz, 1H); 6.64 (d, J=9.9 Hz, 1H); 4.59 (s, 2H); 4.26 (dd, J=8.1, 14.4 Hz, 1H); 4.09 (dd, J=5.7, 14.4 Hz, 1H); 3.96 (overlapped m, 1H); 3.92 (s, 3H); 3.67 (dd, AB syst., J=14.7 Hz, Δ=0.063 ppm, 2H); 3.05 (m, 1H); 2.95 (m, 1H); 2.86 (t, J=10.8 Hz, 1H); 2.00 (m, 1H); 1.91 (m, 1H); 1.48-1.58 (m, 3H); 1.44 (br. s, 1H); 1.08-1.24 (m, 2H).

MS (ESI, m/z): 481.4 [M+H$^+$].

Example 8

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-benzo[1,4]oxazin-3-one Starting from intermediate 6.ii (0.1 g, 0.29 mmol) and 3-oxo-3,4-dihydro-2H-benzo[1,4]oxazine-6-carbaldehyde (commercial; 0.051 g, 1 eq.), the title compound was obtained as a yellowish foam (0.050 g) using the procedures reported in Reference Example 1, step R1.x (reductive amination, 59% yield) and Example 3, step 3.vi (azide reduction, 62% yield). The crude materials were purified by CC using a gradient of DCM-MeOH containing 10% aq. NH$_4$OH as eluent.

MS (ESI, m/z): 480.4 [M+H$^+$].

Example 9

6-({(3R,6S)-6-[(1S)-1-amino-2-(7-methoxy-2-oxo-2H-quinoxalin-1-yl)-ethyl]-tetrahydro-pyran-3-ylamino}-methyl)-4H-pyrido[3,2-b][1,4]thiazin-3-one Starting from (3R,6S)-[6-((2S)-oxiranyl)-tetrahydro-pyran-3-yl]-carbamic acid tert-butyl ester (0.50 g, 2.05 mmol) and 7-methoxy-1H-quinoxalin-2-one (prepared according to WO 2006/134378; 0.4 g, 1.1 eq.) the title compound was obtained as a yellow solid (0.007 g) using the synthetic sequence reported in Example 6. If necessary, the crude materials were purified by CC using appropriate eluents.

MS (ESI, m/z): 497.2 [M+H$^+$].

Example 10

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]thiazin-3-one 10.i. 7-methoxy-1H-[1,8]naphthyridin-2-one To a solution of 7-chloro-1H-[1,8]naphthyridin-2-one (prepared as described in *J. Org. Chem.* (1990), 55, 4744; 5.36 g, 29.68 mmol) in MeOH (98 mL) was added sodium methoxide (25 wt % in MeOH, 161 mL). The resulting solution was stirred at reflux for 15 h. The solvent was removed in vacuo. Water (100 mL) and EA (80 mL) were added. The phases were separated and the aq layer was extracted with EA (8×80 mL). The combined org. layers were washed with brine (50 mL), dried over MgSO$_4$, filtered and evaporated under reduced pressure. The title compound was obtained as a beige solid (5.22 g, 100% yield).

$^1$H NMR (d$_6$DMSO) δ: 11.96 (s, 1H); 7.96 (d, J=8.5 Hz, 1H); 7.81 (d, J=9.4 Hz, 1H); 6.63 (d, J=8.5 Hz, 1H); 6.34 (d, J=9.4 Hz, 1H); 3.90 (s, 3H).

10.ii. 1-[(2S)-2-((2S,5R)-5-amino-tetrahydro-pyran-2-yl)-2-azido-ethyl]-7-methoxy-1H-[1,5]naphthyridin-2-one Starting from intermediate 10.i (1.06 g, 6 mmol) and the compound of Preparation A (1.46 g, 6 mmol), the title compound (0.478 g) was obtained as a colourless foam: using sequentially the procedures reported in Example 3, steps 3.i (epoxide opening, 84% yield), 3.ii (mesylate formation, 100% yield), 3.iii (azide formation, 67% yield) and 3.iv (Boc deprotection, 100% yield). If necessary, the crude reaction mixtures were purified by CC using a suitable eluent. The compound was obtained as a 8:1 mixture of diastereomers.

MS (ESI, m/z): 345.3 [M+H$^+$]

10.iii. 6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]thiazin-3-one Starting from intermediate 10.ii (0.09 g, 0.252 mmol) and 3-oxo-3,4-dihydro-2H-pyrido[3,2-b][1,4]thiazine-6-carbaldehyde (0.050 g, 1 eq.), the title compound was obtained as a white foam (0.084 g) using the procedures reported in Reference Example 1, step R1.x (reductive amination, 81% yield) and Example 3, step 3.vi (azide reduction, 89% yield). The crude materials were purified by CC using a gradient of DCM-MeOH containing 10% aq. NH$_4$OH as eluent.

$^1$H NMR (d$_6$DMSO) δ: 10.82 (s, 1H); 8.01 (d, J=8.5 Hz, 1H); 7.82 (d, J=9.4 Hz, 1H); 7.71 (d, J=7.9 Hz, 1H); 7.07 (d, J=7.9 Hz, 1H); 6.68 (d, J=8.5 Hz, 1H); 6.46 (d, J=9.4 Hz, 1H), 4.51 (dd, J=8.8, 12.6 Hz, 1H); 4.30 (dd, J=4.7, 12.6 Hz, 1H); 3.96 (overlapped m, 1H); 3.93 (s, 3H); 3.71 (dd, AB syst., J=15.0 Hz, Δ=0.062 ppm, 2H); 3.50 (s, 2H); 3.05-3.15 (m, 2H); 2.92 (t, J=10.5 Hz, 1H); 2.43 (overlapped m, 1H); 2.01 (br. s+overlapped m, 2H); 1.49-1.59 (m, 2H); 1.42 (br. s, 1H); 1.11-1.24 (m, 2H).

MS (ESI, m/z): 497.2 [M+H$^+$].

Example 11

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]oxazin-3-one Starting from intermediate 10.ii (0.09 g, 0.252 mmol) and 3-oxo-3,4-dihydro-2H-pyrido[3,2-b][1,4]oxazine-6-carbaldehyde (0.047 g, 1 eq.), the title compound was obtained as a white foam (0.096 g) using the procedures reported in Reference Example 1, step R1.x (reductive amination, 88% yield) and Example 3, step 3.vi (azide reduction, 96% yield). The crude materials were purified by CC using a gradient of DCM-MeOH containing 10% aq. NH$_4$OH as eluent.

$^1$H NMR (d$_6$DMSO) δ (no exchangeable Hs): 8.01 (d, J=8.5 Hz, 1H); 7.82 (d, J=9.4 Hz, 1H); 7.28 (d, J=7.9 Hz, 1H); 6.99 (d, J=7.9 Hz, 1H); 6.68 (d, J=8.5 Hz, 1H); 6.46 (d, J=9.4 Hz, 1H), 4.59 (s, 2H); 4.51 (dd, J=9.1, 12.6 Hz, 1H); 4.29 (dd, J=5.0, 12.6 Hz, 1H); 3.95 (overlapped m, 1H); 3.93 (s, 3H); 3.71 (dd, AB syst., J=15.0 Hz, Δ=0.062 ppm, 2H); 3.05-3.15 (m, 2H); 2.91 (t, J=10.5 Hz, 1H); 2.43 (overlapped m, 1H); 2.01 (m, 1H); 1.49-1.59 (m, 2H); 1.19 (m, 1H).

MS (ESI, m/z): 481.2 [M+H$^+$].

Example 12

1-((1S)-2-amino-2-{(2S,5R)-5-[(2,3-dihydro-[1,4]dioxino[2,3-c]pyridin-7-ylmethyl)-amino]-tetrahydro-pyran-2-yl}-ethyl)-7-methoxy-1H-[1,8]naphthyridin-2-one Starting from intermediate 10.ii (0.100 g, 0.290 mmol) and 2,3-dihydro-[1,4]dioxino[2,3-c]pyridine-7-carbaldehyde (0.048 g, 1 eq.), the title compound was obtained as a white foam (0.096 g) using the procedures reported in Reference Example 1, step R1.x (reductive amination, 58% yield) and Example 3, step 3.vi (azide reduction, 90% yield). The crude materials were purified by CC using a gradient of DCM-MeOH containing 10% aq. NH$_4$OH as eluent.

$^1$H NMR (d$_6$DMSO) δ (no exchangeable Hs): 8.01 (d, J=8.5 Hz, 1H); 7.98 (s, 1H); 7.82 (d, J=9.4 Hz, 1H); 6.91 (s, 1H); 6.68 (d, J=8.5 Hz, 1H); 6.46 (d, J=9.4 Hz, 1H); 4.50 (dd, J=8.8, 12.3 Hz, 1H); 4.24-4.34 (m, 5H); 3.94 (overlapped m, 1H); 3.93 (s, 3H); 3.68 (dd, AB syst., J=15.0 Hz, Δ=0.062 ppm, 2H); 3.04-3.14 (m, 2H); 2.90 (t, J=10.3 Hz, 1H); 2.41 (overlapped m, 1H); 1.97 (m, 1H); 1.47-1.57 (m, 2H); 1.19 (m, 1H).

MS (ESI, m/z): 468.2 [M+H$^+$].

Example 13

1-((1R)-2-amino-2-{4-[(E)-3-(2,5-difluoro-phenyl)-allylamino]-cyclohexyl}-ethyl)-7-methoxy-1H-quinolin-2-one Starting from intermediate 1.B.iv (0.2 g, 0.58 mmol) and (E)-3-(2,5-difluoro-phenyl)-propenal (0.098 g, 1 eq.), the title compound was obtained as a yellowish foam (0.180 g) using the procedures of Reference Example 1, step R1.x (reductive amination, 81% yield) and Example 3, step 3.vi (Staudinger reduction, 80% yield). The crude materials were purified by CC using a gradient of DCM-MeOH containing 10% aq. NH$_4$OH as eluent.

MS (ESI, m/z): 468.3 [M+H$^+$].

Pharmacological Properties of the Invention Compounds

In Vitro Assays

Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results

All Example compounds were tested against several Gram positive and Gram negative bacteria such as *S. aureus*, *E. faecalis*, *S. pneumoniae*, *M catarrhalis*, *A. baumanii*, *E. coli* or *P. aeruginosa*.

Typical antibacterial test results are given in the table hereafter (MIC in mg/l).

| Example No. | MIC for *E. coli* 25922 | MIC for *P. aeruginosa* 27853 |
|---|---|---|
| Ref. Ex. 1 | 0.25 | 0.5 |
| Ref. Ex. 2 | 0.5 | 0.5 |
| 1 | 0.063 | 0.25 |
| 2 | 0.25 | 0.25 |
| 3 | 0.25 | 4 |
| 4 | 0.063 | 2 |
| 5 | 0.125 | 2 |
| 6 | 0.25 | 2 |
| 7 | 1 | 4 |
| 8 | 1 | 4 |
| 9 | 0.25 | 16 |
| 10 | ≦0.031 | 0.5 |
| 11 | 0.5 | 8 |
| 12 | 0.063 | 0.5 |
| 13 | 0.25 | 1 |

The invention claimed is:
1. A compound of formula I

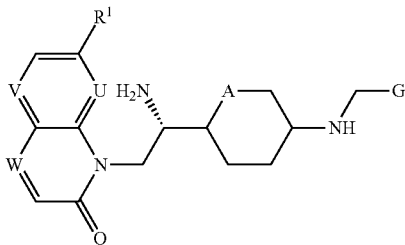

wherein
R¹ represents alkoxy or halogen;
U, V, and W each represents CH, or one of U, V, and W represents N and the others each represents CH;
A represents CH₂ or O;
G is CH=CH-E wherein E represents a phenyl group mono- or di-substituted with halogen, or
G is

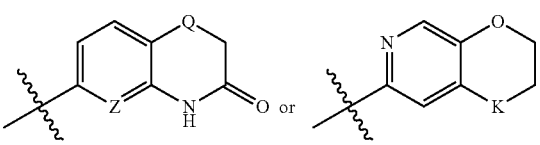

wherein Z represents CH or N, Q represents O or S, and K represents O or S;
or a salt thereof.
2. The compound of formula I according to claim 1, wherein U represents CH, G is CH=CH-E wherein E represents a phenyl group mono- or di-substituted with halogen, or G is a

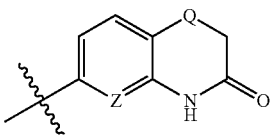

wherein Z represents CH or N and Q represents O or S;
or a salt thereof.
3. The compound of formula I according to claim 1, wherein: U, V, and W each represents CH; U and W each represents CH and V represents N; U and V each represents CH and W represents N; or U represents N and V and W each represents CH; and
R¹ is methoxy or ethoxy;
or a salt thereof.
4. The compound of formula I according to claim 1, wherein
R¹ represents alkoxy or fluorine;
U, V and W each represents CH; U represents CH, one of V and W represents N and the other represents CH; or U represents N and V and W each represent CH;
A represents CH₂ or O;
G is CH=CH-E wherein E represents a phenyl group di-substituted with halogen, or
G is

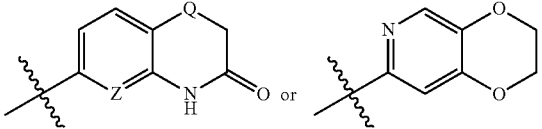

wherein Z represents CH or N and Q represents O or S;
or a salt thereof.
5. The compound of formula I according to claim 1, wherein R¹ represents methoxy;
or a salt thereof.
6. The compound of formula I according to claim 1, wherein A represents CH₂;
or a salt thereof.
7. The compound of formula I according to claim 1, wherein A represents O;
or a salt thereof.
8. The compound of formula I according to claim 1, wherein G is

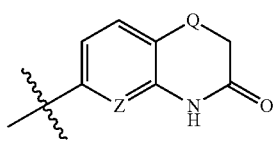

wherein Z represent CH or N and Q represents O or S;
or a salt thereof.
9. The compound of formula I according to claim 1, wherein G represents 3-oxo-3,4-dihydro-2H-benzo[1,4]oxazin-6-yl; 3-oxo-3,4,4a,8a-tetrahydro-2H-pyrido[3,2-b][1,4]thiazin-6-yl; 3-oxo-3,4,4a,8a-tetrahydro-2H-pyrido[3,2-b][1,4]oxazin-6-yl; 2,3-dihydro-[1,4]dioxino[2,3-c]pyridin-7-yl; or 2-(2,5-difluoro-phenyl)-vinyl;
or a salt thereof.
10. The compound of formula I according to claim 1, which is:
  6-(trans-{4-[(1R)-1-amino-2-(7-methoxy-2-oxo-2H-quinolin-1-yl)-ethyl]-cyclohexylamino}-methyl)-4H-pyrido[3,2-b][1,4]thiazin-3-one;
  6-(trans-{4-[(1R)-1-amino-2-(7-methoxy-2-oxo-2H-quinolin-1-yl)-ethyl]-cyclohexylamino}-methyl)-4H-pyrido[3,2-b][1,4]oxazin-3-one;
  6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]oxazin-3-one;
  1-((2S)-2-amino-2-{(2S,5R)-5-[(E)-3-(2,5-difluoro-phenyl)-allylamino]-tetrahydro-pyran-2-yl}-ethyl)-7-methoxy-1H-quinolin-2-one;
  6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]thiazin-3-one;
  6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]thiazin-3-one;
  6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]oxazin-3-one;
  6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-benzo[1,4]oxazin-3-one;

6-({(3R,6S)-6-[(1S)-1-amino-2-(7-methoxy-2-oxo-2H-quinoxalin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,8]naphthyridin-1-yl)-ethyl]-tetrahydro-pyran-3-ylamino}-methyl)-4H-pyrido[3,2-b][1,4]oxazin-3-one;

1-((1S)-2-amino-2-{(2S,5R)-5-[(2,3-dihydro-[1,4]dioxino[2,3-c]pyridin-7-ylmethyl)-amino]-tetrahydro-pyran-2-yl}-ethyl)-7-methoxy-1H-[1,8]naphthyridin-2-one; or 1-((1R)-2-amino-2-{4-[(E)-3-(2,5-difluoro-phenyl)-allylamino]-cyclohexyl}-ethyl)-7-methoxy-1H-quinolin-2-one;

or a salt thereof.

11. The compound of formula I according to claim 1, which is:

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]thiazin-3-one;

6-(trans-{4-[(1R)-1-amino-2-(7-methoxy-2-oxo-2H-quinolin-1-yl)-ethyl]-cyclohexylamino}-methyl)-4H-pyrido[3,2-b][1,4]oxazin-3-one;

6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]oxazin-3-one;

1-((2S)-2-amino-2-{(2S,5R)-5-[(E)-3-(2,5-difluoro-phenyl)-allylamino]-tetrahydro-pyran-2-yl}-ethyl)-7-methoxy-1H-quinolin-2-one;

6-({(3R,6S)-6-[(1S)-1-amino-2-(7-methoxy-2-oxo-2H-quinolin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]thiazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-pyrido[3,2-b][1,4]oxazin-3-one;

6-({(3R,6S)-6-[(1S)-1-amino-2-(7-methoxy-2-oxo-2H-[1,5]naphthyridin-1-yl)-ethyl]-tetrahydro-pyran-3-ylamino}-methyl)-4H-benzo[1,4]oxazin-3-one; or 6-({(3R,6S)-6-[(1S)-1-amino-2-(7-methoxy-2-oxo-2H-quinoxalin-1-yl)-ethyl]-tetrahydro-pyran-3-ylamino}-methyl)-4H-pyrido[3,2-b][1,4]thiazin-3-one;

or a salt thereof.

12. A pharmaceutical composition, comprising the compound of formula I according to claim 1, or a pharmaceutically acceptable salt thereof.

13. A pharmaceutical composition comprising, as an active ingredient, the compound of formula I according to claim 1, or a pharmaceutically acceptable salt thereof, and at least one therapeutically inert excipient.

14. A method for treating a bacterial infection comprising administering the medicament of claim 12.

15. A method for treating a bacterial infection comprising administering the pharmaceutical composition of claim 13 to a subject in need thereof.

* * * * *